US011014945B2

(12) United States Patent
Johnson

(10) Patent No.: US 11,014,945 B2
(45) Date of Patent: May 25, 2021

(54) SULFONYLDIAZOLES AND N-(FLUOROSULFONYL)AZOLES, AND METHODS OF MAKING THE SAME

(71) Applicant: Trinapco, Inc., Oakland, CA (US)

(72) Inventor: Martin Reid Johnson, Piedmont, CA (US)

(73) Assignee: Trinapco, Inc., Oakland, CA (US)

( * ) Notice: Subject to any disclaimer, the term of this patent is extended or adjusted under 35 U.S.C. 154(b) by 0 days.

(21) Appl. No.: 16/841,565

(22) Filed: Apr. 6, 2020

(65) Prior Publication Data

US 2020/0317700 A1 Oct. 8, 2020

Related U.S. Application Data

(60) Provisional application No. 62/836,090, filed on Apr. 19, 2019, provisional application No. 62/830,433, filed on Apr. 6, 2019.

(51) Int. Cl.
| | | |
|---|---|---|
| *C07D 233/58* | (2006.01) | |
| *C07D 235/06* | (2006.01) | |
| *C07D 249/08* | (2006.01) | |
| *C07D 249/18* | (2006.01) | |
| *C07F 7/10* | (2006.01) | |
| *C07D 403/12* | (2006.01) | |

(52) U.S. Cl.
CPC ............... *C07F 7/10* (2013.01); *C07D 233/58* (2013.01); *C07D 235/06* (2013.01); *C07D 249/08* (2013.01); *C07D 249/18* (2013.01); *C07D 403/12* (2013.01)

(58) Field of Classification Search
None
See application file for complete search history.

(56) References Cited

FOREIGN PATENT DOCUMENTS

| CN | 107857730 A | 3/2018 |
| JP | 2002280063 A | 9/2002 |
| WO | 2018157240 A1 | 9/2018 |

OTHER PUBLICATIONS

Thomas, Joice. Regioselective Synthesis of Fluorosulfonyl 1,2,3-Triazoles from Bromovinylsulfonyl Fluoride. Organic Letters, 2018, 20, 3749-3752.*
Zhu, Mingwen. Efficient Synthesis of Biazoles by Aerobic Oxidative Homocoupling of Azoles Catalyzed by Copper(I)/2-pyridonate Catalyic System. Chemical Communications, 2011, 47(48), 12876-12878.*
Kapuriya, Kaushik. Diazoles: Promising and Versatile Class to Design Anti-Microbial Agents. International Journal of PharmTech Research. 2013, 5(2), 568-576.*
Guo, T. et al., "A New Portal to SuFEx Click Chemistry: A Stable Fluorosulfuryl Imidazolium Salt Emerging as an "F-SO2+ "Donor of Unprecedented Reactivity, Selectivity and Scope". Angewandte Chemie, International Edition, Dec. 25, 2017 (Dec. 25, 2017), vol. 57(10), pp. 2605-2610 p. 2604, in particular, Scheme 1 p. 2605, in particular, Figure 1.
Morteza Abdolia and Hamid Saeidian, Journal of Sulfur Chemistry, 2015 vol. 36, No. 5, 556-582, http://dx.doi.org/10.1080/17415993. 2015.1057512 Review Article "Synthesis and reactivity of imidazole-1-sulfonate esters (imidazylates) in substitution, elimination, and metal-catalyzed cross-coupling reactions: a review".
José Francisco Cívicos, Diego A. Alonso, and Carmen Nájera, European Journal of Organic Chemistry 2012 3670-3676, "Oxime-Palladacycle-Catalyzed Suzuki-Miyaura Arylation and Alkenylation of Aryl Imidazolesulfonates under Aqueous and Phosphane-Free Conditions".
Markus Schröter, Tobias Borrmanna, Carsten Knapp, Enno Lork, Rüdiger Mews und Wolf-Dieter Stohrera, Zeitschrift für anorganische und allgemeine Chemie 629 (2003) 1300-1307, "Bis(pyrazolyl)- und Bis(1,2,4)triazolyl-Schwefel-Derivate".
S.A. Shevelev, V.M. Vinogradov, I.L. Dalinger, B.I. Ugrak, A.A. Fainzilberg, and V.I. Fillipov, Bulletin of the Russian Academy of Sciences Division of Chemical Science 41 (1992) 1901-1909, "Reaction of NH-Azoles With O-Fluorosulfonyl, N,N-Difluorohydroxylamine, Synthesis of N-Fluorosulfonylazoles".
Von Heinz A. Staab und Kurt Wendel, Justus Liebigs Annalen der Chemie 694 (1966) 86-90, Aus dem Institut fur Organische Chemie der Universitat Heidelberg Eingegangen am Oct. 15, 1965 1.1 '-Thionyl-di-imidazol und 1.1 '-Sulfuryl-di-imidazol1).
Chris Behme, University of Wisconsin-Madison, WI, USA, N,N'-Sulfuryldiimidazole1 Original Commentary.
E. S. Selezneva et al.; Synthesis of Imidazole and Benzimidazole Derivatives and Their Ability to Induce Recessive Lethal Mutations in *Drosophila* (Fruit Fly); UDC 615.281:547.792.1]. 012.1.07.
Korean Intellectual Property Office (ISA), International Search Report and Written Opinion for PCT/US2020/026957, dated Oct. 7, 2020.

* cited by examiner

*Primary Examiner* — Samantha L Shterengarts
(74) *Attorney, Agent, or Firm* — Duane Morris LLP

(57) ABSTRACT

The present disclosure provides methods for producing N-(fluorosulfonyl)azoles, sulfonyldiazoles, or related derivatives thereof; and the related products including N-(fluorosulfonyl)azoles, sulfonyldiazoles, and related derivatives thereof. For example, an N-(fluorosulfonyl)azole is obtained by reaction of sulfuryl fluoride with an azoles, an azole anion compound, a silylazole, or a combination thereof. Symmetric and asymmetric sulfonyldiazoles are obtained by further reaction of such an N-(fluorosulfonyl) azole with azoles, azole anion compounds, or silylazoles. A sulfonyldiazole can be also produced by reacting sulfuryl fluoride with an azole, a silylazole, or a combination thereof in one pot.

28 Claims, 1 Drawing Sheet

SCHEME 1:
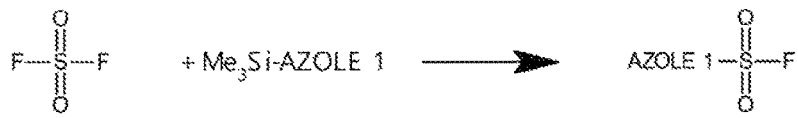
SCHEME 2:
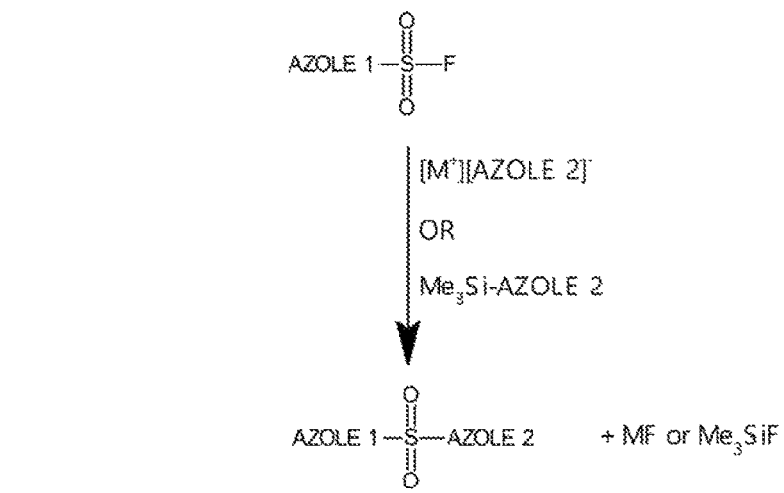
AZOLE 1 = AZOLE 2 = IMIDAZOLE: 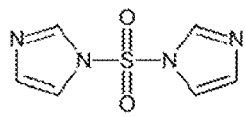
OTHER AZOLES:
Me$_3$Si-AZOLES:
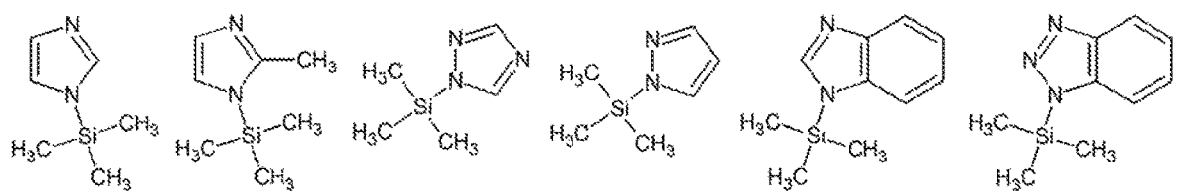

SULFONYLDIAZOLES AND N-(FLUOROSULFONYL)AZOLES, AND METHODS OF MAKING THE SAME

PRIORITY CLAIM AND CROSS-REFERENCE

This application claims the benefit of U.S. Provisional Application No. 62/830,433, filed Apr. 6, 2019, and U.S. Provisional Application No. 62/836,090, filed Apr. 19, 2019, which applications are expressly incorporated by reference herein in their entirety.

FIELD OF THE INVENTION

The disclosure relates to chemical synthesis of azole derivatives generally. More particularly, the disclosed subject matter relates to a process for producing N-(fluorosulfonyl)azoles, sulfonyldiazoles, or related derivatives thereof.

BACKGROUND

N,N'-sulfonyldiimidazole (or 1,1'-sulfonyldiimidazole) has a formula of $SO_2Im_2$, where Im represents imidazolyl. $SO_2Im_2$ is used in about 150 distinct reactions in the literature, and appears in about 300 patents and applications worldwide. Related reviews include: Abdoli, M.; Saeidian, H. Journal of Sulfur Chemistry 2015, 36, 556-582; Behme, C.; Keith, J. M. "N,N'-Sulfuryldiimidazole" in Encyclopedia of Reagents for Organic Synthesis, doi: 10.1002/047084289X.rs141.pub2. $SO_2Im_2$ is also used as an additive for lithium-ion batteries, for example, as disclosed in Japanese Patent Application No. JP2002280063A.

$SO_2Im_2$ was first prepared in 1966 from imidazole and sulfuryl chloride ($SO_2Cl_2$) (Staab, H. A.; Wendel, K. Justus Liebigs Annalen der Chemie 1966, 694, 86-90). Such a method is the most widely used for producing $SO_2Im_2$. $SO_2Im_2$ has also been prepared from N-(trimethylsilyl)imidazole ($Me_3SiIm$) and $SO_2Cl_2$ (Selezneva, E. S.; Belousova, Z. P.; Gusak, L. A.; Zvyagina, E. A.; Purygin, P. P. Pharmaceutical Chemistry Journal 1992, 26, 259-262).

Preparation and use of sulfonylbis(2-methylimidazole) has been reported several times in the literature, and sulfonylbis(2-methylimidazole) are all prepared through the reaction of excess 2-methylimidazole with $SO_2Cl_2$ in dichloromethane. Except $SO_2Im_2$ and sulfonylbis(2-methylimidazole), no other sulfonylbisimidazoles are known.

In addition to $SO_2Im_2$ and sulfonylbis(2-methylimidazole), other sulfonylbisazoles reported in the literature include a few compounds such as sulfonylbis-(1,2,4-triazole) and sulfonyldipyrazole.

Sulfonylbis-(1,2,4-triazole) ($SO_2Tz_2$) and sulfonyldipyrazole ($SO_2Pz_2$) were prepared by reaction of 1-(trimethylsilyl)-1,2,4-triazole ($Me_3SiTz$) and 1-(trimethylsilyl)pyrazole ($Me_3SiPz$), respectively, with $SO_2Cl_2$ in pentane (Schröter, M.; Borrmann, T.; Knapp, C.; Lork, E.; Mews, R.; Stohrer, W.-D. Zeitschrift für anorganische und allgemeine Chemie 2003, 629, 1300-1307). $SO_2Tz_2$ was also prepared using $Me_3SiTz/SO_2Cl_2$ but in toluene.

Preparation of two other sulfonyldipyrazoles as well as several N-fluorosulfonyl-pyrazoles and N-fluorosulfonyl-benzotriazole was also reported. N-(fluorosulfonyl)pyrazole ("$FSO_2Pz$"), several substituted N-(fluorosulfonyl)pyrazoles, and N-(fluorosulfonyl)benzotriazole were first prepared in 1992 by Shevelev et al. (Shevelev, S. A., V. M. Vinogradov, I. L. Dalinger, B. I. Ugrak, A. A. Fainzilberg and V. I. Fillipov, Bulletin of the Russian Academy of Sciences, Division of Chemical Science 1992, 41(10): 1901-1909). Metal salts of azoles were with the compound O-fluorosulfonyl-N,N-difluorohydroxylamine ($FSO_2ONF_2$) under basic homogenous and basic phase transfer conditions, to give the respective N-(fluorosulfonyl)azoles. Cooling below 0° C. was required and yields were mostly below 50%.

Shevelev also described the synthesis of sulfonyl bis (4-chloropyrazole) and sulfonyl bis (4-nitropyrazole), by reaction of a slight excess of the appropriate lithium pyrazolate with the corresponding N-(fluorosulfonyl)pyrazole in acetonitrile. Shevelev also reported that these same two sulfonyldipyrazoles were produced by a disproportionation reaction of the corresponding N-(fluorosulfonyl)pyrazoles. This disproportionation reaction required the use of a soluble, dissolved metal fluoride under aprotic conditions. These were the only two N-(fluorosulfonyl)pyrazoles reported to give sulfonyl bis azoles under either set of conditions; their mild acidity was cited as the enabling cause.

N-(fluorosulfonyl)imidazole ($FSO_2Im$) was first described in a prophetic patent application in the name of Hammami, International Application No. WO2018/157240, which was later abandoned. Hammami predicted the reaction of $SO_2F_2$ with imidazole under basic conditions to give $FSO_2Im$. In 2018, Dong, Guo and their coworkers ("Dong and Guo") reduced the method of Hammani to practice with imidazole, a number of imidazole derivatives, benzimidazole and 2-methylbenzimidazole by infusion of gaseous $SO_2F_2$ into acetonitrile solutions of the azoles with solid sodium carbonate as the base (Dong, J; Yang, Q.; Guo, T.; Zhan, X.; Meng, G.; WO2019/101132 and CN2018/107857730; see also Guo, T.; Meng, G.; Zhan, X.; Yang, Q.; Ma, T.; Xu, L.; Sharpless, K. B.; Dong, J., Angewandte Chemie International Edition 2018, 57, 2605-2610). Dong and Guo did not isolate the fluorosulfonyl azole intermediates; they were left in solution for further reactions, and only minor detail of the chemical composition of the intermediate solutions was described. There was no mention made of any sulfonyl bis azoles in the intermediate solutions prepared by Dong and Guo.

Sulfonyldiimidazole ($SO_2Im_2$) is known to be useful but is quite expensive at present, and its more widespread use is prevented by its high cost. One underlying reason is that all present methods for manufacturing $SO_2Im_2$ utilize $SO_2Cl_2$ as a reactant. $SO_2Cl_2$ is a highly corrosive and toxic liquid, adding additional cost to the related manufacturing processes.

Therefore, it is desirable to have a new safer and cheaper process with more capabilities for producing different types of N-(fluorosulfonyl)azoles, sulfonyldiazoles, or related derivatives thereof.

SUMMARY

The present disclosure provides methods for producing N-(fluorosulfonyl)azoles, sulfonyldiazoles, or related derivatives thereof, and the resulting products.

In accordance with some embodiments, the present disclosure provides methods for obtaining N-(fluorosulfonyl) azoles by reaction of sulfuryl fluoride with azoles, azole anion compounds (e.g., salts), silylazoles, or a combination thereof. The present disclosure also provides methods for obtaining symmetric and asymmetric sulfonyldiazoles by further reaction of N-(fluorosulfonyl)azoles with azoles, azole anion compounds, silylazoles, or a combination thereof. These reactions may be combined in a single pot to produce symmetric sulfonyldiazoles such as sulfonydiimidazoles directly from sulfuryl fluoride. Examples of the azoles used include, but are not limited to, imidazole, pyrazole, 1,2,4-triazole, benzimidazole, benzotriazole, indazole, and their substituted derivatives.

In one aspect, the present disclosure provides one exemplary method for making N,N'-sulfonyldiazole using N-(fluorosulfonyl)azole (Azole 1-SO$_2$F) having a first azole base structure (Azole 1), which is reacted with an azole or an azole anion compound having a second azole base structure (Azole 2). Such a reaction is optionally in the presence of an aprotic solvent to produce an N,N'-sulfonyldiazole (Azole 1-SO$_2$-Azole 2). The N,N'-sulfonyldiazole (Azole 1-SO$_2$-Azole 2) can be isolated.

An azole structure used herein including the first and the second azole base structures may have any suitable azole structures, preferably a protic azole. In some embodiments, the protic azole structure includes hydrogen connected with a nitrogen atom in the azole ring structure. Examples of an azole base structure include, but are not limited to, imidazole, pyrazole, 1,2,4-triazole, benzimidazole, benzotriazole, indazole, 2-methylimidazole, 2-methylbenzimidazole, and 3,5-dimethylpyrazole.

The N,N'-sulfonyldiazole can be symmetric or asymmetric. In some embodiments, the first azole base structure (Azole 1) and the second azole base structure (Azole 2) are the same. The N,N'-sulfonyldiazole is symmetric. In some embodiments, the first azole base structure (Azole 1) and the second azole base structure (Azole 2) are different. The N,N'-sulfonyldiazole is asymmetric.

The reaction or reactions described herein may be optionally in the presence of an aprotic solvent. Examples of suitable aprotic solvent include, but are not limited to, acetonitrile, dichloromethane, ethyl ether, tetrahydrofuran, 2-methyltetrahydrofuran, methylcyclopentyl ether, methyl tert-butyl ether, propionitrile, butyronitrile, toluene, the like, and any combination thereof. The reactants may be suspended or dissolved in the solvent in some embodiments.

In some embodiments, the azole anion compound is an azole anion salt having an cation of a metal. Examples of a suitable metal include, but are not limited to, lithium, sodium, potassium, cesium, magnesium, and a combination thereof.

In some embodiments, the azole anion compound is derived from a free protic azole such as Azole 2 and a metal carbonate. Examples of the metal in the metal carbonate include, but are not limited to, lithium, sodium, potassium, cesium, and magnesium.

In some embodiments, the azole anion compound is derived from the protic azole (Azole 2) and an aprotic base, or the protic azole (Azole 2) as the base.

In some embodiments, the azole anion compound is derived from a silyazole such as a N-(trialkylsilyl)azole having a second azole base structure (Azole 2) in the presence of a basic catalyst. For example, the N-(trialkylsilyl)azole is an N-(trimethylsilyl)azole In some embodiments.

In some embodiments, such a basic catalyst is selected from the group consisting of an anion salt of the protic azole (Azole 2) and a cation of a metal such as lithium, sodium, potassium, cesium, and magnesium. In some embodiments, the basic catalyst is an aprotic organic base or the protic azole (Azole 2). Examples of a suitable aprotic organic base include, but are not limited to, a tertiary amine such as triethylamine, 1,8-diazabicyclo(5.4.0)undec-7-ene (DBU), a phosphazene, and a combination thereof.

In another aspect, the present disclosure provides a method for producing a symmetric N,N'-sulfonyldiazole in a single pot directly. Sulfuryl fluoride (SO$_2$F$_2$) is reacted with an azole or an azole anion compound having a first azole base structure (e.g., Azole 1), optionally in the presence of an aprotic solvent. An N,N'-sulfonyldiazole (Azole 1-SO$_2$-Azole 1) is isolated.

Examples of a suitable azole base structure include, but are not limited to, imidazole, pyrazole, 1,2,4-triazole, benzimidazole, benzotriazole, indazole, 2-methylimidazole, 2-methylbenzimidazole, and 3,5-dimethylpyrazole.

Such a reaction may be performed optionally in the presence of a basic catalyst as described herein.

In some embodiments, the azole anion compound is an azole anion salt having an ion of a metal, which may be lithium, sodium, potassium, cesium, magnesium, or a combination thereof.

In some embodiments, the azole anion compound is derived from a free protic azole such as Azole 1 and a metal carbonate. Examples of the metal in the metal carbonate include, but are not limited to, lithium, sodium, potassium, cesium, and magnesium.

In some embodiments, the azole anion compound is derived from the protic azole (Azole 1) and an aprotic base, or the protic azole (Azole 1) as the base.

In some embodiments, the azole anion compound is derived from a silyazole such as a N-(trialkylsilyl)azole having a second azole base structure (Azole 1) in the presence of a basic catalyst. For example, the N-(trialkylsilyl)azole is an N-(trimethylsilyl)azole.

In another aspect, the present disclosure provides another method for producing N-(fluorosulfonyl)azole, or N,N'-sulfonyldiazole, or both. In such a method, SO$_2$F$_2$ is reacted with a first silyazole having a first azole base structure (Azole 1), optionally in the presence of an aprotic solvent or a basic catalyst or both, to provide a N-(fluorosulfonyl)azole (Azole 1-SO$_2$F). The N-(fluorosulfonyl)azole may be used as a reaction intermediate, or optionally isolated, for example, through distillation. The silyazole may be an N-(trialkylsilyl)azole such as an N-(trimethylsilyl)azole.

As described herein, an azole base structure may have any suitable structure, for example, imidazole, pyrazole, 1,2,4-triazole, benzimidazole, benzotriazole, indazole, 2-methylimidazole, 2-methylbenzimidazole, and 3,5-dimethylpyrazole. Examples of a suitable aprotic solvent and a suitable basic catalyst are described above.

In some embodiments, the basic catalyst is an aprotic organic base, or the protic azole such as Azole 1 as a base. In some embodiments, the basic catalyst is selected from the group consisting of an anion salt of a protic azole (Azole 1) and an ion of a metal selected from the group consisting of lithium, sodium, potassium, cesium, and magnesium. Examples of an aprotic organic base include, but are not limited to, a tertiary amine such as triethylamine, 1,8-diazabicyclo(5.4.0)undec-7-ene (DBU), a phosphazene, and a combination thereof.

In some embodiments, the method may further comprise reacting the N-(fluorosulfonyl)azole (Azole 1-SO$_2$F) with a second silyzole or an azole anion salt having a second azole base structure (Azole 2), optionally in the presence of an aprotic solvent or an aprotic catalyst, to provide an N,N'-sulfonyldiazole (Azole 1-SO$_2$-Azole 2), which may be symmetric or asymmetric. For example, the first and the second azole base structures are the same, and sulfuryl fluoride (SO$_2$F$_2$) is reacted with a first silyazole in one pot directly to provide a symmetric sulfonyldiazole. N,N'-sulfonyldiazole may be isolated or further purified through crystallization.

Examples of the N,N'-sulfonyldiazole described herein include, but are not limited to, N,N'-sulfonyldiimidazole ($SO_2Im_2$), 1,1'-sulfonylbis(2-methyl-1H-imidazole), 1-(1H-imidazole-1-sulfonyl)-1H-pyrazole ($ImSO_2Pz$), and sulfonylbis(3,5-dimethylpyrazole).

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

FIG. 1 illustrates exemplary methods for preparing a N-(fluorosulfonyl)azole and/or an N,N'-sulfonyldiazole in accordance with some embodiments. Scheme 1 illustrates an exemplary method comprising reacting sulfuryl fluoride ($SO_2F_2$) with a silylazole having a first azole base structure (Azole 1) to generate a N-(fluorosulfonyl)azole (Azole 1-$SO_2F$) in accordance with some embodiments. Scheme 2 illustrates an exemplary method comprising reacting a N-(fluorosulfonyl)azole (Azole 1-$SO_2F$) with an azole or an azole anion compound having a second azole base structure (Azole 2) to provide an N,N'-sulfonyldiazole (Azole 1-$SO_2$-Azole 2) in accordance with some embodiments.

DETAILED DESCRIPTION

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. Thus, for example, a reference to "a ring structure" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The terms "protic" and "aprotic" used herein refer to the presence or absence of a hydrogen atom bonded to a nitrogen or oxygen atom. The term "aprotic solvent" thus refers to a solvent that has no —OH or —NH moieties. For example, ethyl ether is an aprotic solvent and ethanol is a protic solvent. Azoles can also be protic or aprotic. Examples of aprotic azoles are thiazole and oxazole. Examples of protic azoles include, but are not limited to, imidazole, pyrazole, 1,2,4-triazole, benzimidazole, benzotriazole, indazole, 2-methylimidazole, 2-methylbenzimidazole, and 3,5-dimethylpyrazole. Unless indicated otherwise, references to "azole" made herein will be understood to encompass protic azoles, not aprotic azoles.

Unless indicated otherwise, references to "silylazole" made herein refer to a protic azole where only the protic hydrogen atom has been replaced by a trialkylsilyl group. For example, 1-(trimethylsilyl)imidazole is a silylazole. Azoles with a silicon atom bonded to other ring atoms are excluded from the definition of a silylazole as used herein. For example, 2-(trimethylsilyl)imidazole is not a silylazole as defined herein.

Unless indicated otherwise, references to "pot" made herein refer to a flask or autoclave used to conduct a reaction, or to hold the transferred contents of a reaction.

Unless indicated otherwise, references to "low pressure" made herein refer to a reaction condition at or below atmospheric pressure and the term "high pressure" refers to a reaction condition above atmospheric pressure. The term "under pressure" is also used to describe unspecified high pressure.

The term "iced" used herein refers to the process of cooling a pot in a mixture of ice and water, to a temperature range of 0 to +4° C.

The term "GCMS" used herein refers to the analysis method of gas chromatography-mass spectroscopy. Charge-to-mass values are reported with the term "m/e" followed by an integer. Mass detection was by electron impact.

The present disclosure provides methods for producing N-(fluorosulfonyl)azoles, sulfonyldiazoles, or related derivatives thereof; and the related products including N-(fluorosulfonyl)azoles, sulfonyldiazoles, and related derivatives thereof.

In some embodiments, the present disclosure enables low-cost manufacture of sulfonyldiazoles such as $SO_2Im_2$, not only by elimination of $SO_2Cl_2$ from the process stream but also from simplified, nonaqueous workup procedures.

The inventor has found that the prophetic patent application of Hammami is inaccurate when metallic bases strong enough to give imidazolate are used in the reaction of imidazole with sulfuryl fluoride ($SO_2F_2$); sulfonyldiimidazole ($SO_2Im_2$) predominates, not $FSO_2Im$. This finding extends to other azoles besides imidazole.

The inventor has also found that under modified conditions of the method used by by Dong and Guo, $SO_2Im_2$ can be made the dominant product, with a purified yield as high as 82%.

The inventor has additionally found that N-(fluorosulfonyl)azoles are reactive beyond the limited findings of Shevelev. $FSO_2Im$ reacts with imidazole to give $SO_2Im_2$. $SO_2F_2$ can be used instead to obtain $SO_2Im_2$ from imidazole in a single pot.

$SO_2F_2$ reacts with azole anion salts in the presence of a solvent. These salts may be either suspended in an aprotic solvent, or generated continuously in small amounts by reaction of the azole with a metal carbonate, to give symmetric sulfonyldiazoles.

N-(fluorosulfonyl)azoles react with azole anion salts, optionally suspended in an aprotic solvent, or generated continuously in small amounts by reaction of the azole with a metal carbonate, to give both symmetric and asymmetric sulfonyldiazoles.

N-(fluorosulfonyl)azoles react with silylazoles, optionally in the presence of a basic catalyst, or solvent, or both, to give symmetric and asymmetric sulfonyldiazoles.

Sulfuryl fluoride gas reacts with silylazoles, optionally in the presence of a basic catalyst, or solvent, or both, to give either N-(fluorosulfonyl)azoles or symmetric sulfonyldiazoles preferentially, depending on the reaction conditions.

Purification of the N-(fluorosulfonyl)azole products of the present invention is best accomplished by distillation. Purification of the sulfonyldiazole products of the present invention is best accomplished by recrystallization.

Many embodiments of the present Invention use all-liquid reactants, or readily form all-liquid pots, and are suitable for continuous, large-scale production in a flow reactor.

In a broader aspect, the inventors has found at least three exemplary methods for producing N-(fluorosulfonyl)azoles, sulfonyldiazoles, or related derivatives thereof.

In the first exemplary method, as illustrated in Scheme 2 of FIG. 1, a N-(fluorosulfonyl)azole having a first azole base structure (Azole 1-$SO_2$F) is reacted with an azole or an azole anion compound, which has a second azole base structure (Azole 2), to produce an N,N'-sulfonyldiazole (Azole 1-$SO_2$-Azole 2). Such a reaction is optionally performed in the presence of an aprotic solvent. The N,N'-sulfonyldiazole (Azole 1-$SO_2$-Azole 2) can be isolated.

The first and the second azole base structures may have any suitable azole structures, preferably a protic azole structure. In some embodiments, the protic azole structure include hydrogen connected with a nitrogen atom in the azole ring structure. Examples of an azole base structure include, but are not limited to, imidazole such as benzimidazole, pyrazole, 1,2,4-triazole, benzotriazole, indazole, indazole, 2-methylimidazole, 2-methylbenzimidazole, and 3,5-dimethylpyrazole. The descriptions apply to all the azole structures in each exemplary method described herein.

The N,N'-sulfonyldiazole can be symmetric or asymmetric. In some embodiments, the first azole base structure (Azole 1) and the second azole base structure (Azole 2) are the same. The N,N'-sulfonyldiazole is symmetric. In some embodiments, the first azole base structure (Azole 1) and the second azole base structure (Azole 2) are different. The N,N'-sulfonyldiazole is asymmetric.

The reaction or reactions described herein may be optionally in the presence of an aprotic solvent. Examples of suitable aprotic solvent include, but are not limited to, acetonitrile, dichloromethane, ethyl ether, tetrahydrofuran, 2-methyltetrahydrofuran, methylcyclopentyl ether, methyl tert-butyl ether, propionitrile, butyronitrile, toluene, the like, and any combination thereof. The reactants may be suspended or dissolved in the solvent in some embodiments.

The reaction or reactions described herein may be optionally in the presence of a basic catalyst. Examples of a suitable basic catalyst include, but are not limited to, an aprotic organic base, a metal hydride, a metal alkoxide, a metal hydroxide, a metal carbonate, alkyllithium, and a combination thereof. Examples of a suitable metal include, but are not limited to, an alkali metal (e.g., Na, K) and alkaline earth metal.

In some embodiments, the azole anion compound is an azole anion salt having an ion of a metal. Examples of a suitable metal include, but are not limited to, lithium, sodium, potassium, cesium, magnesium, and a combination thereof.

In some embodiments, the azole anion compound is derived from a free azole such as Azole 2 and a metallic base selected such as a metal hydride, a metal alkoxide, a metal hydroxide, a metal carbonate, alkyllithium, and a combination thereof. In some embodiments, the azole anion compound is derived from a free protic azole such as Azole 2 and a metal carbonate. Examples of the metal in the metal carbonate include, but are not limited to, lithium, sodium, potassium, cesium, and magnesium.

In some embodiments, the azole anion compound is derived from the protic azole (Azole 2) and an aprotic base, or the protic azole (Azole 2) as the base.

In some embodiments, the azole anion compound is derived from Azole 2 as a free azole and an aprotic organic base. Examples of a suitable aprotic organic base include, but are not limited to, triethylamine, 1,8-diazabicyclo(5.4.0)undec-7-ene (DBU), a phosphazene, and a combination thereof.

In some embodiments, the azole anion compound is derived from a silyazole having a second azole base structure (e.g., Azole 2) in the presence of a basic catalyst. In some embodiments, the azole anion compound is derived from a silyazole such as a N-(trialkylsilyl)azole having a second azole base structure (Azole 2) in the presence of a basic catalyst. For example, the N-(trialkylsilyl)azole is an N-(trimethylsilyl)azole In some embodiments. In some embodiments, such a basic catalyst is selected from the group consisting of an anion salt of the protic azole (Azole 2) and a cation of a metal such as lithium, sodium, potassium, cesium, and magnesium. In some embodiments, the basic catalyst is an aprotic organic base or the protic azole (Azole 2). Examples of a suitable aprotic organic base include, but are not limited to, a tertiary amine such as triethylamine, 1,8-diazabicyclo(5.4.0)undec-7-ene (DBU), a phosphazene, and a combination thereof.

Examples of a suitable N,N'-sulfonyldiazole include, but are not limited to, N,N'-sulfonyldiimidazole ($SO_2Im_2$), 1,1'-sulfonylbis(2-methyl-1H-imidazole), 1-(1H-imidazole-1-sulfonyl)-1H-pyrazole ($ImSO_2Pz$), and sulfonylbis(3,5-dimethylpyrazole). N,N'-sulfonyldiazole can be isolated or further purified through recrystallization.

In the second exemplary method, a symmetric N,N'-sulfonyldiazole is produced in a single pot directly. Sulfuryl fluoride ($SO_2F_2$) is reacted with an azole or an azole anion compound having a first azole base structure (e.g., Azole 1), optionally in the presence of an aprotic solvent as described herein. N,N'-sulfonyldiazole (Azole 1-$SO_2$-Azole 1) can be isolated.

As described above, examples of a suitable azole base structure include, but are not limited to, imidazole, pyrazole, 1,2,4-triazole, benzimidazole, benzotriazole, indazole, indazole, 2-methylimidazole, 2-methylbenzimidazole, and 3,5-dimethylpyrazole. Such a reaction may be performed optionally in the presence of a basic catalyst as described above.

In some embodiments, as described above, the azole anion compound is an azole anion salt having an ion of a metal, which may be lithium, sodium, potassium, cesium, magnesium, or a combination thereof.

In some embodiments, the azole anion compound is derived from a free protic azole such as Azole 1 and a metal carbonate. Examples of the metal in the metal carbonate include, but are not limited to, lithium, sodium, potassium, cesium, and magnesium. In some embodiments, the azole anion compound is derived from the protic azole (Azole 1) and an aprotic base, or the protic azole (Azole 1) as the base. In some embodiments, the azole anion compound is derived from a silyazole such as a N-(trialkylsilyl)azole having a second azole base structure (Azole 1) in the presence of a basic catalyst. For example, the N-(trialkylsilyl)azole is an N-(trimethylsilyl)azole.

In the third exemplary method, as illustrated in Schemes 1 and 2 of FIG. 1, N-(fluorosulfonyl)azole, or N,N'-sulfonyldiazole, or both can be produced. $SO_2F_2$ is reacted with a first silyazole having a first azole base structure (Azole 1) to provide a N-(fluorosulfonyl)azole (Azole 1-$SO_2F$). The silyazole might be a N-(trialkylsilyl)azole such as an N-(trimethylsilyl)azole. Such a reaction is performed optionally in the presence of an aprotic solvent or a basic catalyst or both. The N-(fluorosulfonyl)azole may be used as a reaction intermediate, or optionally isolated, for example, through solvent distillation. As described above, an azole base structure may have any suitable structures, for example, imidazole, pyrazole, 1,2,4-triazole, benzimidazole, benzotriazole, indazole, indazole, 2-methylimidazole, 2-methylbenzimidazole, and 3,5-dimethylpyrazole. Examples of a suitable aprotic solvent include, but are not limited to, acetonitrile, dichloromethane, ethyl ether, tetrahydrofuran, 2-methyltetrahydrofuran, methylcyclopentyl ether, methyl tert-butyl ether, propionitrile, butyronitrile, toluene, and a combination thereof. Examples of a suitable basic catalyst include those described above. In some embodiments, the basic catalyst is an aprotic organic base, or the protic azole such as Azole 1 as a base. In some embodiments, the basic catalyst is selected from the group consisting of an anion salt of a protic azole (Azole 1) and an ion of a metal selected from the group consisting of lithium, sodium, potassium, cesium, and magnesium. Examples of an aprotic organic base include, but are not limited to, a tertiary amine such as triethylamine, 1,8-diazabicyclo(5.4.0)undec-7-ene (DBU), a phosphazene, and a combination thereof.

The N-(fluorosulfonyl)azole (Azole 1-$SO_2F$) may be further reacted with a second silyzole or an azole anion salt having a second azole base structure (Azole 2), optionally in the presence of an aprotic solvent or an aprotic catalyst, to provide an N,N'-sulfonyldiazole (Azole 1-$SO_2$-Azole 2). Azole 1 and Azole 2 may be the same or different, and the N,N'-sulfonyldiazole may be symmetric or asymmetric. For example, the first and the second azole base structures are the same, and sulfuryl fluoride ($SO_2F_2$) is reacted with a first silyazole in one pot directly to provide a symmetric sulfonyldiazole. N,N'-sulfonyldiazole may be isolated or further purified through crystallization.

Examples of the N,N'-sulfonyldiazole include, but are not limited to, N,N'-sulfonyldiimidazole ($SO_2Im_2$), 1,1'-sulfonylbis(2-methyl-1H-imidazole), 1-(1H-imidazole-1-sulfonyl)-1H-pyrazole (Im$SO_2$Pz), and sulfonylbis(3,5-dimethylpyrazole).

Reactions with Sulfuryl Fluoride ($SO_2F_2$)

In some embodiments, where $SO_2F_2$ is a reactant, and a sulfonyl bis azole is the desired product, the mole ratio of $SO_2F_2$ to the azole or azole-containing precursor is preferably close to 1:2. In some embodiments, where $SO_2F_2$ is a reactant, and a sulfonyl bis azole is the desired product, if the mole ratio of $SO_2F_2$ to the azole or azole-containing precursor is greater than 1:2, increased amounts of the intermediate N-(fluorosulfonyl)azole can be found at the expense of product, particularly when the $SO_2F_2$ is added rapidly, and the intermediate does not further react in a timely fashion.

In some embodiments, where $SO_2F_2$ is a reactant, $SO_2Im_2$ is the desired product, and an aprotic organic base is used, the mole ratio of $SO_2F_2$ to imidazole is preferably less than 1:2, more preferably about 1:4.

In some embodiments, where $SO_2F_2$ is a reactant, and an N-(fluorosulfonyl)azole is the desired product, the mole ratio of $SO_2F_2$ to the azole or azole-containing precursor is preferably 1:1, or greater. In some embodiments, where $SO_2F_2$ is a reactant, and an N-(fluorosulfonyl)azole is the desired product, the use of mole ratios greater than 1:1 can result in improved yields of N-(fluorosulfonyl)azole.

In some embodiments, where $SO_2F_2$ is a reactant, and an N-(fluorosulfonyl)azole is the desired product, lower temperatures can be preferred.

In some embodiments, where $SO_2F_2$ is a reactant, and a sulfonyldiazole is the desired product, higher temperatures can be preferred.

Reaction of $SO_2F_2$ with Imidazole: Sulfonyldiimidazole ($SO_2Im_2$)

In some embodiments, $SO_2F_2$ is introduced at low pressure into a sealed vessel containing an acetonitrile solution of imidazole and a suspension of a metallic base such as a metal carbonate under anhydrous conditions. The dissolved imidazole exists in equilibrium with its anion, presumably at or near the surface of the solid carbonate. Some freely dissolved imidazolate may also be present. Addition of $SO_2F_2$ to the pot results in an exothermic reaction. When potassium carbonate ($K_2CO_3$) is used (Example 1), the addition of $SO_2F_2$ is very rapid, even at low pressure. When sodium carbonate ($Na_2CO_3$) is used (Example 2), the addition proceeds more slowly at low pressure. The reaction may be preferably performed at temperatures from +25° C. to +50° C. Pot loads as high as 2 molar imidazole, or higher, may be employed, although in acetonitrile a pot load of 2 molar or less is more preferable as the product $SO_2Im_2$ remains dissolved and the pot is more easily emptied. Additionally, 2 molar imidazole is fully dissolved in acetonitrile only above about 20° C. At the end of the reaction, the insoluble salts are separated and the solvent removed. Residual salts are eliminated by dissolving the crude solid in dichloromethane, filtration, and evaporation of the solvent. Recrystallization from ≥3 mL/g ethanol gives the product. High pressure may be used if the pot is well cooled; however, the use of low pressure means better safety, and also enables the use of large reactors for the same capital cost as a much smaller autoclave. In addition the use of low pressure allows for better temperature control and more precise endpoints, thus minimizing any excess of added $SO_2F_2$.

In some embodiments, imidazole is fully deprotonated prior to addition of $SO_2F_2$, and the resultant imidazolate salt is used. Suitable imidazolate cations include lithium, sodium, potassium, cesium, and magnesium. Sodium imidazolate is preferred (Example 41). It is readily prepared in anhydrous form from imidazole and sodium hydroxide by heating under dynamic vacuum to 200° C. and <50 Pa. This treatment gives a friable solid which readily forms a fine suspension in acetonitrile. When the pot is evacuated prior to addition of $SO_2F_2$, the addition proceeds rapidly at low pressure. In some embodiments, conducted at low pressure, when a fully deprotonated metal imidazolate is used and the pot properly degassed prior to addition of $SO_2F_2$, the pot pressure near the endpoint can drop below the vapor pressure of the pure solvent.

In some embodiments, where imidazole is allowed to react with $SO_2F_2$, organic bases are used stoichiometrically (Examples 9 and 10). In these Examples, the organic bases are the weak base triethylamine and the strong base 1,8-diazabicyclo(5.4.0)undec-7-ene (DBU). In some embodiments, where imidazole is allowed to react with $SO_2F_2$, and $SO_2Im_2$ is the desired product, triethylamine can be preferred as a base. It is less expensive than DBU. Triethylamine hydrofluoride readily dissolves in ethanol, and is easily separated from crude pot solids with an ethanol wash. The remaining solid is pure product. In some embodiments, where imidazole is allowed to react with SO2F2, and SO2Im2 is the desired product, the use of dichloromethane and triethylamine can be preferred.

In some embodiments, where imidazole is allowed to react with $SO_2F_2$, $SO_2Im_2$ is the desired product, and triethylamine is used as the organic base, an excess of imidazole can be beneficial. In Example 44, a 1:2:2 mole ratio of $SO_2F_2$/imidazole/triethylamine was used, and the product $SO_2Im_2$ obtained in 37% yield. In Example 45, under nearly identical conditions, a 1:4:2 mole ratio of $SO_2F_2$/imidazole/triethylamine was used, and a 69% yield of $SO_2Im_2$ was obtained. Example 9 is also relevant. Example 9 was conducted in acetonitrile, a 1:2.2:2.2 mole ratio of $SO_2F_2$/imidazole/triethylamine was used, and a yield of 40% $SO_2Im_2$ was obtained. The inventor believes that the lower yields of examples 44 and 9, compared to Example 45, arise from dissolved fluoride, which is a byproduct of the reaction. Dissolved fluoride can form hydrogen bonds with the N—H of imidazole, and the resulting complex resists deprotonation by the tertiary amine. The addition of more imidazole creates unbound N—H hydrogen. This unbound N—H hydrogen can then deprotonate and react with the intermediate $FSO_2Im$ to give $SO_2Im_2$. Azoles other than imidazole can behave similarly.

In some embodiments, reactors made of metal or plastic are preferred over glass, which corrodes in the presence of fluoride.

In some embodiments, where other azoles besides imidazole are used, the azole can be reacted with $SO_2F_2$ to produce symmetric bis azoles. For example, metal salts of pyrazole, 1,2,4-triazole (Example 22), benzimidazole, and benzotriazole can be used to produce $SO_2Pz_2$, $SO_2Tz_2$, Sulfonylbis(benzimidazole), and sulfonylbis(benzotriazole) respectively. Metal salts of many other azoles can also be used if they can be obtained in anhydrous form. Some substituted pyrazoles, imidazoles, 1,2,4-triazoles, benzimidazoles, and benzotriazoles can be readily deprotonated with sodium or potassium hydroxide, and the like, and reacted with $SO_2F_2$ to give symmetric sulfonyl bis azoles. Many metal salts of azoles are not easily obtained by simple reaction of the azole with a metal hydroxide; however, a metal-hydride-derived azolate can be used instead. In some embodiments, where a metal azolate is used and derived from a metal hydride or other metallic strong base, the use of a silylazole instead of a metal azolate salt can be preferred.

In some embodiments, when the pot contains ionic components such as metal salts, the crude pot solid obtained by removal of the volatile components of the reaction may be taken up in a less-polar solvent (such as dichloromethane) and filtered. This process can remove all traces of metal fluoride and other ionic components of the reaction, leaving a product with only traces of free azole as an impurity. These azoles are often volatile enough to be sublimed from the dried filtrate, giving a pure product as the residue.

Reaction of $SO_2F_2$ with Silylazoles

In some embodiments, $SO_2F_2$ is allowed to react with an N-silylazole. The reaction may be conducted without solvent or catalyst, but either or both can be preferred. Both mono- and bis-adducts are usually found together in the reactor, but one or the other can be produced preferentially, depending on the reaction conditions and the reactant itself.

In some embodiments, where $SO_2F_2$ is allowed to react with an N-silylazole, trimethylsilylazoles are preferred.

In some embodiments, when a silylazole is used as a reactant, all of the reactants and catalysts are soluble in a volatile, less-polar solvent (such as dichloromethane) which is easily removed. This can be preferred, particularly when a distilled product is desired.

Reaction of $SO_2F_2$ with Silylazoles. No Catalyst

In some embodiments, where $SO_2F_2$ reacts with a silylazole, a catalyst is not required, provided the temperature is high enough. When the reaction between $SO_2F_2$ and $Me_3SiIm$ (2 molar in acetonitrile) and was conducted in an autoclave at a mole ratio of 1:2 at temperatures up to 60° C. for 19 hours, it gave some $SO_2Im_2$ but mainly $FSO_2Im$ and reactants. When this same pot was resealed and brought to 100° C. in the autoclave for an additional 14 hours, the reaction was substantially complete and $SO_2Im_2$ was recovered in 73% yield. See Example 7.

Acetonitrile is a preferred hot solvent for the reaction of both $SO_2F_2$ and $FSO_2Im$ with $Me_3SiIm$ in the absence of catalyst. Butyronitrile was also tried as a hot solvent (Example 8) without catalyst and found to be less preferred. Half a mole each of $FSO_2Im$ and $Me_3SiIm$, in 500 mL butyronitrile at reflux for 15 hours (121° C.) only gave minor conversion to $SO_2Im_2$, in contrast to the full conversion of $FSO_2Im$ using acetonitrile at the lesser temperature of 100° C. for about the same time (Example 7).

Reaction of $SO_2F_2$ with Silylazoles. Weak Base as Catalyst

In some embodiments, where $SO_2F_2$ reacts with a silylazole, a weak base is used, and the major product is an N-(fluorosulfonyl)azole. A mole ratio of 1:1 $SO_2F_2$/silylazole, or greater, is preferred. For these particular embodiments, triethylamine is preferred as the weak base. Triethylamine is inexpensive, volatile and easily removed during workup. For some embodiments, the mole ratio of weak base to silylazole can range from 1 mole % to 100 mole % or greater, more preferably 10-50 mole %. For some embodiments, when the silylazole is trimethylsilylimidazole ($Me_3SiIm$), the major product is N-(fluorosulfonyl)imidazole ($FSO_2Im$). In experimental Example 3, $Me_3SiIm$ and $SO_2F_2$ are the reactants, triethylamine is the catalyst, the reaction takes place without solvent at high pressure in an autoclave, and $FSO_2Im$ is obtained in a 94% yield. In some embodiments, a silylazole and $SO_2F_2$ are the reactants, triethylamine is the catalyst, the reaction takes place in a solvent below atmospheric pressure, and a fluorosulfonyl azole is the major product. See Example 23.

Reaction of $SO_2F_2$ with Silylazoles. Strong Base as Catalyst

In some embodiments, where $SO_2F_2$ reacts with a silylazole, a strong base is used as the catalyst, and a symmetric sulfonyl bis azole is the major product. In those particular embodiments involving the reaction of $SO_2F_2$ with a silylazole, where a symmetric SO2-azole bis adduct is the desired product, the mole ratio of $SO_2F_2$ to silylazole is preferably close to 1:2. When the silylazole is $Me_3SiIm$, the major product is $SO_2Im_2$. Strong bases include a metal salt of the azole from which the silylazole is derived, metal hydrides such as sodium or lithium hydride, metal alkoxides or hydroxides, DBU, and phosphazene bases. DBU is preferred. DBU is miscible with polar solvents and all of the neat liquid silylazoles tested to date. DBU is a very potent catalyst in the reaction of both $SO_2F_2$ and $FSO_2$-azoles with silylazoles. In some embodiments, the mole ratio of DBU to silylazole can range from 0.01:1 (1%) down to $5 \times 10^{-5}$:1 (0.005%). Higher mole ratios can be used but offer no benefit. Lower mole ratios, below $5 \times 10^{-5}$, can be used in certain cases. The minimum mole ratio depends on the silylazole. It is unclear whether or not the DBU is reacting directly with the silylazole or with traces of free azole, but in any event a small amount of free azole can be added to the pot. To date this has not been necessary.

One exception found under strong base and ambient temperature conditions is the reaction of $SO_2F_2$ with 1-trimethylsilyl-3,5-dimethylpyrazole in DBU/acetonitrile (Example 30). The bis adduct was not found. The mono adduct 3,5-dimethyl-1H-pyrazole-1-sulfonyl fluoride $FSO_2PzMe_2$ was produced, in high yield (95%).

In some embodiments, where $SO_2F_2$ reacts with a silylazole, DBU is the catalyst, the reaction is conducted in dichloromethane at a low temperature, and an $FSO_2$-azole mono adduct is the major product. See Examples 38, 39, and 40.

Reaction of $FSO_2$-Azoles with Azoles, Azole Salts and Silylazoles

In some embodiments, a fluorosulfonyl azole (such as $FSO_2Im$) reacts with an azole, a metal azolate salt, or a silylazole, and a symmetric or asymmetric sulfonyl bis azole is produced. When the azole groups are the same, a symmetric bis azole is obtained. When the azole groups are different, an asymmetric bis azole is obtained.

In some embodiments, a fluorosulfonyl azole (such as $FSO_2Im$) reacts with an azole, and a sulfonyl bis azole results. In some embodiments, where a fluorosulfonyl azole reacts with an azole, and a sulfonyl bis azole is the product, a stoichiometric amount of an organic base (such as triethylamine) can be used. In some embodiments, where a fluorosulfonyl azole reacts with an azole, and a sulfonyl bis azole is the product, a solvent can be used. See Example 43.

In some embodiments involving the reaction of a fluorosulfonyl azole with a silylazole, neither catalyst nor solvent is necessary for the reaction to proceed, but either a catalyst, a solvent, or both, may be used. In some embodiments involving the reaction of a fluorosulfonyl azole with a silylazole, when no catalyst is employed, the reaction proceeds at higher temperatures. The use of higher temperatures across many embodiments requires extended reaction times, tends to produce dark pots, and is less preferred.

By contrast, in some embodiments involving the reaction of a fluorosulfonyl azole with a silylazole in the absence of solvent, when DBU is employed, lower temperatures can be used, the reactions take only a few hours at 50° C., near colorless pots are found at the end of the reaction, and yields approaching quantitative can be had. The reaction takes place as low as 40° C. See Examples 33, 36, and 37.

In some embodiments involving the reaction of a fluorosulfonyl azole with a silylazole in the presence of DBU, a solvent is used, and the reaction is conducted at or below room temperature. Acetonitrile and dichloromethane are preferred solvents.

In some embodiments, many different solvents, or mixtures of solvents, can be used. In acetonitrile, if the product is a solid, it often precipitates from the pot in high purity. Dichoromethane dissolves some sulfonyldiazoles ($SO_2Im_2$, $SO_2Pz_2$, $SO_2Tz_2$) freely. Traces of free azoles can be removed by recrystallization of the crude product in a suitable solvent, or sublimation, or both. See Examples 8, 17, 31, and 32.

In all embodiments, the best yields are obtained by the use of anhydrous reactants and solvents throughout the entire process.

EXPERIMENTAL

All reactions were conducted in a fume hood. Low pressure additions were conducted with a pressure gate, which regulates the pot pressure. When the pot pressure dropped below the set pressure, more gas was added until the set pressure was reached. The pressure gate display was also used as a manometer. In most of the Examples involving $SO_2F_2$, both mono and bis adducts were produced. In a few of the Examples, both products were isolated and yields given, but usually only the yield of the desired product is given. Reaction progress was often monitored by GCMS, which is definitive for the identity of each peak in the trace, but only qualitative for its relative amount in the pot. When a liquid product was obtained, removal of more-volatile dichloromethane or acetonitrile was omitted from the Example, and only the product boiling point is reported. Silylazoles were prepared by reaction of the azole with hexamethyldisilazane.

Example 1

Sulfonyldiimidazole ($SO_2Im_2$). A 1 Liter 4-necked roundbottom flask was charged with anhydrous, powdered $K_2CO_3$ (124 g, 0.9 moles) and a solution of imidazole in acetonitrile (2 molar, 300 mL, 0.6 moles). The pot contents were magnetically stirred and evacuated to constant static pressure (9.7 kPa). $SO_2F_2$ (30.5 g, 0.3 moles) was added at 93 kPa over five minutes and the pot rose from 24 to 40° C. After stirring another 36 minutes the pot had dropped to 30° C./49 kPa. The pot was infilled with nitrogen to atmospheric pressure and the gas inlet replaced with a mercury bubbler. Progress of the reaction was monitored by GCMS. The pot was brought to 40° C. for two hours, then brought to 50° C. for three hours, after which the reaction was deemed complete although both imidazole and $FSO_2Im$ were still present in the GCMS trace. The pot contents were filtered and the solid washed with copious amounts of warm acetonitrile. The combined filtrates were concentrated to dryness giving a solid, which was taken up in dichloromethane (400 mL), filtered, and the clear colorless filtrate again concentrated to dryness. The solid so obtained (57 g) was recrystallized from ethanol (200 mL) to give the product $SO_2Im_2$ (48 g, 0.24 moles, 82%). M.p. 139-140° C. GCMS single peak, m/e 198.

Example 2

Sulfonyldiimidazole. A 1 Liter 4-necked roundbottom flask was charged with anhydrous, powdered $Na_2CO_3$ (128 g, 1.2 moles) and a solution of imidazole in acetonitrile (2 molar, 300 mL, 0.6 moles). The pot was placed in an ambient water bath, and the pot contents were magnetically stirred and evacuated to constant static pressure (11 kPa). $SO_2F_2$ (30 g, 0.3 moles) was added at 93 kPa over 42 minutes at 24° C. After stirring another 73 minutes the pot had dropped to 23° C./25 kPa. The pot was infilled with nitrogen to atmospheric pressure and the gas inlet replaced with a mercury bubbler. Progress of the reaction was monitored by GCMS. The pot was brought to 38-40° C. for 12 hours, then brought to 50° C. for three hours, after which the reaction was deemed complete although both imidazole and $FSO_2Im$ were still present in the GCMS trace. The pot contents were filtered and the solid washed with warm acetonitrile (300 mL). The combined filtrates were concentrated to dryness, giving a solid, which was taken up in dichloromethane (400 mL), filtered, and the clear colorless filtrate again concentrated to dryness. The solid so obtained (52 g) was recrystallized from ethanol (180 mL) to give the product $SO_2Im_2$ (39 g, 0.195 moles, 67%). M.p. 139-140° C. GCMS single peak, m/e 198. A second crop was obtained from the concentrated filtrate (3 g, 15 mmole, 5%) m.p. 138-139° C. GCMS single peak, m/e 198. Total yield, 42 g, 0.21 moles, 72%.

Example 3

1H-imidazole-1-sulfonyl fluoride ($FSO_2Im$). A 600 mL autoclave was charged with 1-trimethylsilyl-1H-imidazole ($Me_3SiIm$, 151 g, 1.1 moles) and triethylamine (30 mL), sealed, iced, and evacuated to constant static pressure (2.9 kPa). $SO_2F_2$ (123 g, 1.21 moles) was added rapidly under pressure. The stirred pot was then held at 25° C. for three days and the pot pressure dropped from 1275 kPa to 212 kPa. The pot was stirred another day and the pressure stayed around 212 kPa. The pot was then vented, sparged with nitrogen, and the pot contents distilled at 56° C./3.3 kPa to give the product $FSO_2Im$ (153 g, 1.02 moles, 94%.) $FSO_2Im$ supercools readily, m.p. 31.5° C.

Example 4

Sulfonyldiimidazole. A 500 mL two-necked roundbottom flask was charged with 1H-imidazole-1-sulfonyl fluoride ($FSO_2Im$, 60 g, 0.4 moles), imidazole (27 g, 0.4 moles), $K_2CO_3$ (80 g, 0.58 moles), and acetonitrile (250 mL). The pot contents were magnetically stirred at 50-55° C. for eight hours, then cooled, giving crystals. The pot was warmed up briefly to 70° C., filtered, and the solids washed with hot acetonitrile. The combined filtrates were concentrated to dryness. The resulting solid was taken up in dichloromethane (400 mL), filtered, and the clear colorless filtrate again concentrated to dryness. The solid so obtained (74 g) was recrystallized from ethanol to give the product $SO_2Im_2$ (63 g, 0.32 moles, 80%). M.p.=139-140° C.

Example 5

Sulfonyldiimidazole. A 600 mL autoclave was charged with 1-(trimethylsilyl)imidazole ($Me_3Si$, 66 g, 0.47 moles) acetonitrile (300 mL), and 1,8-Diazabicyclo[5.4.0]undec-7-ene (DBU, 1 gram, 7 mmoles). The autoclave was sealed, cooled to –25° C., and evacuated to constant static pressure (133 Pa). The manometer was isolated and $SO_2F_2$ (23.7 g, 0.23 moles) was introduced from an inverted lecture bottle as a liquid, resulting in a rapid temperature increase to –2° C. After a minute, the manometer was re-engaged and the pressure was found to be 164 kPa. The autoclave was again cooled to –25° C. and the pressure dropped to 61 kPa. After eight more minutes the pressure had dropped to 42 kPa. The autoclave was warmed to +50° C. over sixteen minutes, resulting in a pressure increase to 102 kPa. After a few more minutes the pressure had dropped to 87 kPa. The autoclave was cooled to 1° C./26 kPa with an ice bath and the volatile byproduct fluorotrimethylsilane ($FSiMe_3$) was distilled into a cold trap. The autoclave was then warmed to room temperature, infilled with nitrogen, and opened to reveal a clear colorless liquid and a white solid. The solid was collected by filtration, rinsed with acetonitrile, and dried under dynamic vacuum to give the product $SO_2Im_2$ (23.3 g) as a white microcrystalline solid, m.p. 139-141° C. The filtrate was concentrated and cooled overnight at 4° C. to give a second crop, which was filtered, washed with ethanol, and dried to give an additional 15.4 g, m.p. 140-142° C. Total yield, 38.7 g (0.195 moles, 85%).

Example 6

Sulfonyldiimidazole. A 600 mL autoclave was charged with 1-(trimethylsilyl)imidazole (110 g, 0.78 moles) acetonitrile (300 mL), and 1,8-diazabicyclo[5.4.0]undec-7-ene (DBU, 0.32 g, 2 mmol), sealed, stirred, cooled to an indicated temperature of –1° C. in an ice water bath, and evacuated to constant static pressure (4.7 kPa). The manometer was isolated and $SO_2F_2$ (38.4 g, 0.38 moles) was added to the ice-cooled pot at 93 kPa over a period of seven minutes, during which time the pot temperature rose to 26° C. After 27 more minutes, the pot dropped to 2° C./32 kPa and the volatile contents distilled into a cold trap (48 g). The pot was then evacuated to constant static pressure and warmed to 60° C., infilled with nitrogen, and opened to reveal a clear colorless liquid. This liquid was decanted and refrigerated (+4° C.) for a few hours. The solid so obtained was collected by filtration, rinsed with acetonitrile (20 mL), and dried under dynamic vacuum overnight, giving the product (69 g, 0.35 moles, 92%), m.p. 139-140° C.

Example 7

Sulfonyldiimidazole. A 600 mL autoclave was charged with $Me_3SiIm$ (66.4 g, 0.47 moles) and acetonitrile (300 mL), cooled to 0° C. and evacuated to constant static pressure (5 kPa). $SO_2F_2$ (66.4 g, 0.47 moles) was added at 160 kPa over a period of six minutes at +1 to +5° C., then stirred at 30° C. for about 10½ hours. The pot pressure had dropped to 43 kPa. The pot was infilled with nitrogen, opened, and the pot contents analyzed by GCMS. $SO_2Im_2$ was found along with much $Me_3SiIm$ and $FSO_2Im$. The pot was resealed and held at 60° C. for 19 hours, cooled and opened. The amount of $SO_2Im_2$ by GCMS increased but substantial $Me_3SiIm$ and $FSO_2Im$ remained. The pot was then resealed and held at 100° C. for 13½ hours, cooled, and opened. GCMS showed only traces of $FSO_2Im$ and $Me_3SiIm$. The pot contents were iced, filtered, and the solid so obtained washed with acetonitrile and dried under dynamic vacuum overnight to give the product $SO_2Im_2$ as colorless crystals, 33.5 g (0.17 moles, 73%), m.p.=139.5-140.5° C.

Example 8

Sulfonyldiimidazole. A 1-necked 1 liter roundbottom flask was charged with $FSO_2Im$ (75 g, 0.5 moles), $Me_3SiIm$ (71 g, 0.5 moles), and butyronitrile (500 mL). The flask was magnetically stirred and the clear colorless contents brought to reflux under nitrogen with a bubbler to monitor efflux of gas. After 15 hours at reflux (121° C.), the pot was still clear, but quite dark. The pot was cooled to 15° C. and remained clear. The pot contents were analyzed by GCMS. Some $SO_2Im_2$ was detected along with large amounts of reactants. To this cooled, clear, dark pot was added DBU (0.2 g, 0.001 moles) and the pot stirred while insulated with an unplugged mantle. After 22 minutes, precipitate began to form and the pot had warmed to 28° C., where it remained for another 40 minutes, then began to cool. After three more hours the pot supernatant was analyzed by GCMS. The $Me_3SiIm$ was completely gone and $SO_2Im_2$ was the dominant peak in the GC trace. The solvent was removed and pot contents dried under dynamic vacuum giving a solid (99 g), which was recrystallized from ethanol (340 mL total volume) and dried under dynamic vacuum to give the product $SO_2Im_2$ as off-white crystals (84 g, 0.42 moles, 85%). M.p.=139.5-140° C.

Example 9

Sulfonyldiimidazole. A 600 mL autoclave was charged with imidazole (60 g, 0.88 moles), triethylamine (90 g, 0.89 moles) and acetonitrile (250 mL), cooled, and evacuated to constant static pressure (12 kPa) at 18° C. $SO_2F_2$ (41 g, 0.4 moles) was added rapidly to the stirred pot from an inverted lecture bottle. The pot pressure rose to 900 kPa, then rapidly declined. After nine minutes the pot had dropped to 29 kPa and the temperature had risen to 30° C. The pot was then held at 80-83° C. for an hour, cooled to about 50° C., and opened to reveal a clear yellow liquid. The liquid was transferred to a beaker, stirred, and iced, giving a precipitate. The solid so obtained was collected by filtration, stirred with chilled ethanol (200 mL total volume), again filtered, and dried under dynamic vacuum to give the product $SO_2Im_2$ (32 g, 0.16 moles, 40%). M.p.=140-141.5° C.

Example 10

Sulfonyldiimidazole. A 600 mL autoclave was charged with imidazole (40 g, 0.59 moles), DBU (89.5 g, 0.59 moles) and acetonitrile (300 mL), cooled and evacuated to constant static pressure (13 kPa). $SO_2F_2$ (30 g, 0.3 moles) was added at 26-53 kPa over a period of five minutes at a temperature range of 22-32° C., then stirred at 21-27° C. for an hour; the pressure had dropped to 14.5 kPa. The pot was infilled with nitrogen, opened, and analyzed by GCMS. Analysis was impaired by interference from the DBU peak, but both $SO_2Im_2$ and $FSO_2Im$ were detected. The pot was resealed and evacuated, and held at 80° C. for two hours. The pot was cooled, infilled with nitrogen, and opened to reveal a dark yellow mixture. The pot contents were transferred to a beaker and placed in a freezer overnight. The solid so obtained was collected by filtration, rinsed with acetonitrile, and dried under dynamic vacuum for a day to give the product $SO_2Im_2$ (31.3 g, 160 mmol, 54%). M.p.=139-140.5° C.

Example 11

Fluorosulfonylimidazole. A 600 mL autoclave was charged with $Me_3SiIm$ (90 g, 0.64 moles) and imidazole (0.5 g, 7 mmol) sealed, cooled, and evacuated to constant static pressure (266 Pa). $SO_2F_2$ (67 g, 0.65 moles) was added and the pot stirred under pressure for 15 h at 12-20° C. The pot was vented and the contents distilled at 51-53° C./1.8 kPa to give the product $FSO_2Im$ (57 g, 0.38 moles, 59%).

Example 12

Fluorosulfonylimidazole. A 600 mL autoclave was charged with $Me_3SiIm$ (86.5 g, 0.62 moles) and acetonitrile (300 mL), sealed, cooled, and evacuated to constant static pressure (9.6 kPa). $SO_2F_2$ (63.5 g, 0.62 moles) was added under pressure over seven minutes and the pot stirred at 17-25° C. After 12 hours pot pressure had dropped below atmospheric and the volatile $FSiMe_3$ byproduct distilled into a dry ice trap. The pot was infilled with nitrogen and the contents distilled at 54-55° C./2.66 kPa to give the product $FSO_2Im$ (54.8 g, 0.365 moles, 59%).

Example 13

Fluorosulfonylimidazole. A 600 mL autoclave was charged with $Me_3SiIm$ (87.9 g, 0.63 moles), triethylamine (6.4 g, 0.06 moles) and acetonitrile (300 mL), sealed, cooled, and evacuated to constant static pressure (3.5 kPa). $SO_2F_2$ (100 g, 0.98 moles) was added under pressure over four minutes and the pot stirred at 8-17° C. for 45 minutes. The volatile $FSiMe_3$ byproduct was distilled into a dry ice trap under static vacuum and the pot was infilled, opened, and distilled at 52° C./2.66 kPa to give the product $FSO_2Im$ (80 g, 0.53 moles, 85%). The liquid product readily supercools, m.p. 31.5° C. Pot residue, 4.5 g.

Example 14

Fluorosulfonylimidazole. A 600 mL autoclave was charged with $Me_3SiIm$ (87.9 g, 0.63 moles), and acetonitrile (300 mL), sealed, cooled, and evacuated to constant static pressure (7.6 kPa). $SO_2F_2$ (101.6 g, 0.995 moles) was added under pressure over 21 minutes and the pot stirred at +1 to +14° C. for three hours. The pot was vented, sparged with nitrogen, and opened. GCMS revealed unreacted $Me_3SiIm$. The pot contents were twice distilled at 52° C./2.66 kPa to give the product $FSO_2Im$ (63.3 g, 0.42 moles, 67%).

Example 15

Fluorosulfonylimidazole. A 600 mL autoclave was charged with $Me_3SiIm$ (87.9 g, 0.63 moles), imidazole (4.3 g, 0.063 moles) and acetonitrile (300 mL), sealed, cooled, and evacuated to constant static pressure (4.3 kPa). $SO_2F_2$ (96.6 g, 0.95 moles) was added at 344 kPa over 15 minutes and the pot stirred at 25° C. for 17 hours to 94 kPa. The volatile $FSiMe_3$ byproduct was distilled into a dry ice trap. The pot was opened and the contents distilled at 49° C./2.66 kPa to give the product (56.4 g, 0.38 moles, 60%). A considerable amount of solid remained in the still.

Example 16

Sulfonyldiimidazole. A 600 mL autoclave was charged with $Me_3SiIm$ (87.9 g, 0.63 moles), imidazole (4.3 g, 0.063 moles) and acetonitrile (300 mL), sealed, cooled, and evacuated to constant static pressure (4.9 kPa). $SO_2F_2$ (69.8 g, 0.68 moles) was added at 482 kPa over five minutes. The temperature rose from −3° C. to +14° C. and the pressure rapidly dropped from 482 kPa to about 180 kPa. The pot was stirred for 37 more minutes at 22° C., then vented, sparged with nitrogen, and opened. The pot contents were transferred and the volatile components removed at 55° C./5.3 kPa, leaving behind a solid which was stirred with ethanol, rinsed and dried to give the product $SO_2Im_2$ (32 g, 0.16 moles, 51%). m.p. 139.5-141° C.

Example 17

Sulfonyldiimidazole. To a 500 mL flask was added $Me_3SiIm$ (69.2 g, 0.49 moles) DBU (1.1 g, 0.007 moles) and acetonitrile (150 mL). A solution of $FSO_2Im$ (70 g, 0.47 moles) in acetonitrile (100 mL) was added dropwise over 22 minutes at 26 to 53° C. and stirred 9 hours at ambient temperature. The next day the pot contents were filtered, rinsed with acetonitrile (20 mL), and dried under dynamic vacuum to give the product $SO_2Im_2$ (81.2 g, 0.41 moles, 88%), m.p.=141-143° C.

Example 18

1,1'-Sulfonylbis(2-methyl-1H-imidazole). A 600 mL autoclave was charged with N-(trimethylsilyl)-2-methylimidazole (151 g, 0.98 moles), DBU (0.32 g, 2 mmoles) and acetonitrile (250 mL), sealed, cooled, and evacuated to constant static pressure (5.7 kPa). $SO_2F_2$ (50.5 g, 0.495 moles) was added at 0 to +10° C./73 kPa over 20 minutes. The pot was kept on ice for ten more minutes, warmed to 31° C. and byproduct $FSiMe_3$ removed by distillation under static vacuum. The pot was infilled with nitrogen and opened to reveal a clear yellow solution, which was concentrated on a rotary evaporator giving a damp solid. This was rinsed three times with 2-propanol and dried under dynamic vacuum to give the product sulfonylbis(2-methylimidazole) (82.4 g, 0.36 moles, 74%), m.p.=95-95.5° C. The 2-propanol filtrates were concentrated and a second crop collected (12.4 g, 55 mmol, 11%), m.p.=95-95.5° C. Total yield, 95 g (0.42 moles, 86%). GCMS m/e 226.

Example 19

2-Methyl-1H-imidazole-1-sulfonyl fluoride. A 600 mL autoclave was charged with N-(trimethylsilyl)-2-methylimidazole (100 g, 0.65 moles), triethylamine (6 g, 60 mmoles) and acetonitrile (250 mL), sealed, iced, and evacuated to constant static pressure (6.9 kPa). $SO_2F_2$ (66.2 g, 0.65 moles) was added at 0 to +7° C./344 kPa over five minutes. The ice bath was removed and the pot stirred for 18 hours at 12-14° C. The $FSiMe_3$ byproduct was removed by distillation under static vacuum. The pot was infilled with nitrogen and opened to reveal a clear yellow liquid which was distilled at 51° C./2.0 kPa to give the product (94 g, 0.57 moles, 88%) as a clear colorless liquid. GCMS m/e 164.

Example 20

Sulfonylditriazole ($SO_2Tz_2$). A 600 mL autoclave was charged with 1-(trimethylsilyl)-1,2,4-triazole ($Me_3SiTz$) (141 g, 1 mole), DBU (0.32 g, 2 mmoles) and acetonitrile (250 mL), sealed, cooled, and evacuated to constant static pressure (5.7 kPa). $SO_2F_2$ (50.5 g, 0.495 moles) was added at +4 to +16° C. and 73 kPa over 40 minutes in two successive additions. The pot was kept iced for three minutes, warmed to 31° C. and byproduct $FSiMe_3$ removed by distillation under static vacuum. The pot was infilled with nitrogen and opened to reveal a clear yellow solution with suspended needles. The needles were collected by filtration, rinsed with 2-propanol, and dried under dynamic vacuum to give the product $SO_2Tz_2$ (81 g, 0.4 moles, 81%). M.p.=142-143° C.; sealed and remelted, 137-139° C. Lit. m.p.=98° C. GCMS m/e 201 ([M+H]$^+$, very small).

Example 21

Sulfonylditriazole. A 1 liter 4-necked flask was equipped with a stir egg, thermometer, stoppers, and a vacuum adapter, and charged with trimethylsilyltriazole ($Me_3SiTz$, 248 g, 1.75 moles), DBU (0.32 g, 2 mmoles) and dichloromethane (250 mL). The pot was cooled with a dry ice-acetone bath to −25° C. and evacuated to constant static pressure (1.5 kPa). $SO_2F_2$ (105 g, 1.02 moles) was added to the magnetically stirred pot at −11 to −18° C./80 kPa over 30 minutes, in two portions, the first portion being insufficient as the pot had become too thick to stir. This result was unexpected. $SO_2Tz_2$ was not anticipated to be the preferred product at this temperature, and only 30 g $SO_2F_2$ had been added. Additional dichloromethane (250 mL) was added and the addition recommenced. The pot was recooled and reevacuated, and more $SO_2F_2$ added (total 105 g, 1.02 moles) at −50 to −30° C./80 kPa over three minutes, after which the pot pressure dropped. The pot was warmed to +4° C. giving a static pressure of 47 kPa. Further warming resulted in gas efflux and much thicker pot contents. The pot became unstirrable and another 100 mL dichloromethane was added to facilitate stirring. The pot was refluxed until the temperature had reached 38° C., then cooled. The product was collected by suction filtration, rinsed with a little dichloromethane, and the fine, flocculent solid placed in a 50° C. oven for 6½ hours, giving the product $SO_2Tz_2$ (159 g, 0.79 moles, 90%) m.p.=137-139° C. Recrystallization from ethanol (1.8 L) gave a more crystalline product, 140 g, m.p. 138-139° C. Concentration of the ethanolic filtrate gave an oil with the odor of sulfur dioxide.

Example 22

Sulfonylditriazole. A solution of 1,2,4-triazole (34.54 g, 0.5 moles in 1.00N aqueous NaOH (500 mL) in a 1-necked 1 liter roundbottom flask was concentrated to dryness on a rotary evaporator, then placed under high vacuum and kept for 40 minutes at 200° C./8 Pa using an oil bath. A friable solid was obtained (46.6 g, 102%). The flask was cooled, infilled with nitrogen and a stir egg added. The pot was closed with a rubber seal, and acetonitrile (500 mL) transferred in via cannula. The seal was quickly replaced with a vacuum adapter and the pot pumped down to 10 kPa when it began to boil. The pot was placed in a water bath at about 20° C., stirred, and $SO_2F_2$ (40 g, 0.38 moles) added over 18 minutes at 67 kPa. The pot was unsealed, a condenser added, and the pot contents gently warmed to expel most of the excess $SO_2F_2$ gas. The remainder of gas was expelled by a short reflux. The pot was then concentrated to dryness, the contents taken up in dichloromethane, and filtered. The clear colorless liquid was concentrated to dryness and the residual solid melted at 109-113° C. To the flask was added an extension, the flask fully immersed in a water bath, and placed under dynamic vacuum at 80° C. until no further sublimation was observed into the extension. The unsublimed solid was the product $SO_2Tz_2$ (31 g, 0.155 moles, 62%. The product exhibited a very sharp melting point, 140° C.

Example 23

1H-1,2,4-Triazole-1-sulfonyl fluoride ($FSO_2Tz$). A 3 L 4-necked roundbottom flask was charged with $Me_3SiTz$ (105 g, 0.74 moles), triethylamine (6.6 g, 65 mmoles) and acetonitrile (1 Liter), magnetically stirred, sealed, cooled to −20° C. and evacuated until the pot began to boil. $SO_2F_2$ (158 g, 1.5 moles) was added below atmospheric pressure over 30 minutes at −20 to −15° C., keeping the pressure below atmospheric. A mercury column was used to measure pressure. The pot was held at −15 to −25° C. for 30 minutes and warmed to +16° C., when it began to outgas through the mercury column. Warming was continued to +25° C. and the pot sparged with nitrogen for 30 minutes. The product distilled at 51° C./2.0 kPa (57.8 g, 0.38 moles, 52%) as a clear colorless liquid with an acrid odor. Pot solids about 26 g. The product $FSO_2Tz$ was redistilled (48° C./1.7 kPa) with a loss of 0.8 g. (51% overall yield). GCMS m/e 151.

Example 24

1H-1,2,4-Triazole-1-sulfonyl fluoride. A 600 mL autoclave was charged with $Me_3SiTz$ (210 g, 1.5 moles) and triethylamine (40 mL), sealed, iced, and evacuated to constant static pressure (4.4 kPa). $SO_2F_2$ (153 g, 1.5 moles) was added rapidly under pressure from an inverted lecture bottle having a 7 kPa check valve in-line. The inverted lecture bottle was left attached and open to the pot. The stirred pot was then held at 25° C. for 24 hours. The pot pressure dropped from 1200 kPa to 580 kPa and did not drop further after another 24 hours. The lecture bottle was sealed off, the pot vented and sparged with nitrogen, and opened to reveal a nearly empty vessel. The lecture bottle was examined and found to be filled with liquid, evidently the result of a faulty check valve. Both pot and bottle were emptied into a flask and distilled at 53° C./1.95 kPa to give the product $FSO_2Tz$ (150 g, 1 mole, 66%). GCMS m/e 151. Distillation residue, 27 g solid.

Example 25

Fluorosulfonylimidazole. A 500 mL 3-necked roundbottom flask was equipped with a stir egg, thermometer, gas inlet, and rubber seal, and charged with $Me_3SiIm$ (70.6 g, 0.5 moles), DBU (0.3 g, 2 mmoles) and dichloromethane (310 g). The seal was replaced with a stopper. The pot was iced and evacuated to constant static pressure (17 kPa). $SO_2F_2$ (57 g, 0.56 moles) was added at 80 kPa and +2 to +15° C. over 18 minutes, then warmed to expel volatiles and distilled at 56° C./3.3 kPa to give the product $FSO_2Im$ (54.3 g, 78 mmol, 72%). Pot solids 15.5 g.

Example 26

Sulfonyldipyrazole ($SO_2Pz_2$). A 1 Liter 4-necked roundbottom flask was charged with N-trimethylsilylpyrazole ($Me_3SiPz$, 138 g, 0.98 moles), DBU (0.3 g, 2 mmol) and acetonitrile (500 mL), magnetically stirred, iced and evacuated to constant static pressure (4.8 kPa). $SO_2F_2$ (51.4 g, 0.5 moles) was added at +2 to +18° C./40 kPa over 15 minutes. At the endpoint the pressure was 28 kPa. The pot was warmed up to +27° C., infilled with nitrogen to atmospheric pressure, and stirred overnight at room temperature, about 8° C. The crystals which formed were separated by pressure filtration under nitrogen and dried in a stream of nitrogen to give the product $SO_2Pz_2$ (59 g, 0.3 moles, 59%). M.p. 138.5-139.5° C. The filtrate was concentrated and a second crop obtained, (22 g, 0.11 mole, 22%) M.p.=138.5-139° C. Total yield, 80.5 g (0.41 moles, 81%). The filtrate still had considerable product but a third crop was not collected. GCMS m/e 198.

Example 27

Sulfonyldipyrazole ($SO_2Pz_2$). A 1 Liter 1-necked roundbottom flask was charged with $Me_3SiPz$ (184 g, 1.3 moles), DBU (0.2 g, 1.5 mmol) and acetonitrile (500 mL), magnetically stirred, iced and evacuated to constant static pressure (4.1 kPa). $SO_2F_2$ (67.8 g, 0.66 moles) was added at 40 kPa over a period of 50 minutes. The temperature was not monitored. At the endpoint the pressure was 31 kPa. After 10 minutes the pot, already containing solids, was infilled with nitrogen to atmospheric pressure, and stirred overnight at room temperature (12° C.) with an attached bubbler. The crystals which formed were separated by pressure filtration under nitrogen and dried in a stream of nitrogen to give the product $SO_2Pz_2$ (86 g, 0.43 moles, 66%). M.p. 138.5-139.5° C. The filtrate was concentrated to dryness (43 g) and recrystallized from acetonitrile (100 mL) to give a second crop (34 g, 0.17 mole, 22%) M.p.=137-138.5° C. Total yield, 121 g (0.61 moles, 92%).

Example 28

Sulfonylbis(benzotriazole). A 1 Liter 1-necked roundbottom flask was charged with trimethylsilylbenzotriazole (192 g, 1 mole), DBU (0.3 g, 2 mmol) and acetonitrile (525 mL), magnetically stirred, iced and evacuated to constant static pressure (4.1 kPa). $SO_2F_2$ (52.1 g, 0.5 moles) was added at 93 kPa over a period of 27 minutes. The temperature was not monitored. Solids appeared immediately upon addition and the pot turned bright yellow. The pot became thick with solid. The pot was stirred overnight, allowing it to vent, and warmed in a bath, causing color change from yellow to orange. The solid was separated by pressure filtration under nitrogen and rinsed under pressure with acetonitrile (200 mL) which removed most of the color from the solid. The dark orange filtrate was discarded and the solid dried under a stream of nitrogen to give a crude product (150 g, 0.5 moles, 100%), m.p. 167° C. (decomposed).

Example 29

Sulfonylbis(benzimidazole). A 1 Liter 1-necked roundbottom flask was charged with dissolved solid trimethylsilylbenzimidazole (37.6% w/w in acetonitrile, 506 g, 1 mole), more acetonitrile (200 mL), and DBU (0.3 g, 2 mmol). The pot was magnetically stirred, iced, and evacuated to constant static pressure (3.2 kPa). $SO_2F_2$ (51.4 g, 0.5 moles) was added at 67 kPa over a period of seven minutes. The temperature was not monitored. Solids appeared after four minutes, producing a viscous suspension. After another 28 minutes on ice the pot pressure stabilized at 23 kPa. The pot was then warmed up to 45-50° C. for about an hour, allowing it to vent. The solid was separated by pressure filtration under nitrogen and dried under a stream of nitrogen, giving the product sulfonylbis(benzimidazole) (142 g, 0.48 moles, 95%). M.p. 190-193° C.

Example 30

N-(Fluorosulfonyl)-3,5-dimethypyrazole. A 1 liter 1-necked pear shaped flask was equipped with a Claisen adapter, rubber seal, and gas inlet, and charged via cannula with 1-(trimethylsilyl)-3,5-dimethylpyrazole (169.2 g, 1.04 moles), acetonitrile (500 mL) and DBU (0.25 g, 1.6 mmoles). The rubber seal was replaced with a thermometer and the pot was iced, cooled to constant static pressure (3 kPa), and addition of $SO_2F_2$ commenced (+1 to +3° C.) at a gated pressure of 33 kPa. The addition was slow; after 20 minutes only 10 g $SO_2F_2$ had been added. After an additional 15 minutes at 46 kPa, the addition stalled and only 16 g $SO_2F_2$ had been added. The pot was then re-evacuated, infilled with nitrogen, and an additional 0.5 g DBU added. The pot was again evacuated to 3 kPa/2° C. and addition recommenced at a gated pressure of 33 to 40 kPa. Addition was more facile and exothermic than before (+2 to +8° C.) and after about an hour an additional 106 g $SO_2F_2$ had been added, emptying the lecture bottle of its $SO_2F_2$. The pot was then warmed up to 55-60° C., allowing it to vent, then distilled at 58-59° C./0.27 kPa to give the product N-(fluorosulfonyl)-3,5-dimethylimidazole (171 g, 0.96 moles, 95%). GCMS m/e 178.

Example 31

1-(1H-Imidazole-1-sulfonyl)-3,5-dimethyl-1H-pyrazole ($ImSO_2PzMe_2$). A 500 mL 1-necked roundbottom flask was equipped with a Claisen adapter, rubber seal, and gas inlet, and charged via cannula with 1-(trimethylsilyl)-3,5-dimethylpyrazole (50 g, 0.28 moles), $FSO_2Im$ (43.5 g, 0.29 moles) in acetonitrile (500 mL total acetonitrile). DBU (0.28 g, 2 mmoles) was injected and the pot stirred for 2 hours at 25° C. Conversion was only partial (GCMS) and more DBU (0.36 g, 2 mmoles) added. Stirring was continued for a day and a half at room temperature and silylazole was still present. Another 1.4 g $FSO_2Im$ was added to the pot. The pot was stirred under nitrogen during a ten day hiatus. The pot was then concentrated to dryness at 50° C./0.5 kPa, giving an oil (67 g) which solidified on cooling. The solid was taken up in hot ethanol (200 mL) and refrigerated overnight. The crystals which formed were separated by pressure filtration under nitrogen, rinsed with ethanol (50 mL), and dried in a stream of nitrogen to give the product $ImSO_2PzMe_2$ (55.6 g, 0.25 moles, 88%), m.p.=100-101° C. GCMS did not give a peak at m/e 226, but a peak at 162, corresponding to an SO2-extruded coupling product.

Example 32

Sulfonyldiimidazole. A 500 mL, 1-necked pear shaped flask was equipped with a stir bar and a gas-thermometer adapter, and flushed with nitrogen through the thermometer opening. The flask was charged through the opening via cannula, against the nitrogen flow, with FSO2Im (53.4 g, 0.36 moles), $Me_3SiIm$ (50.6 g, 0.36 moles) and acetonitrile (200 mL). The thermometer was placed and the pot iced. When the pot had cooled to 10° C. the thermometer was removed and DBU (0.3 g, 2 mmoles) added through the opening. The thermometer was replaced. After two minutes precipitate was observed (25° C.). The pot was taken out of ice and the temperature rose to 42° C. after two more minutes, then fell. The pot was again iced to 10° C. and as a result the suspension agglomerated. The agglomerate was broken up, the pot stirred another 3 hours at room temperature, and allowed to sit overnight. The following day the pot was concentrated to dryness dry and the solid so obtained was recrystallized from ethanol (200 mL). The crystals which formed were separated by pressure filtration under nitrogen and dried in a stream of nitrogen to give the product $SO_2Im_2$ (60 g, 0.3 moles, 85%) m.p.=139-141° C. A second crop was collected from the concentrated filtrate (6.2 g, 0.03 moles, 9%). M.p.=140-141° C. Total yield, 66 g, 0.33 moles, 94%.

Example 33

Sulfonyldiimidazole. A 500 mL, 3-necked roundbottom flask with a stir egg, rubber seal, thermometer, and gas inlet was charged with $FSO_2Im$ (66 g, 0.44 moles) and $Me_3SiIm$ (63.5 g, 0.45 moles), and cooled to 10° C. DBU (0.36 g, 5 mmoles) was injected. The pot was placed in a 50° C. bath, and the gas efflux monitored. Gas efflux began when the pot reached 40° C.; the pot then heated endogenously to 60° C. over 20 minutes, when solids appeared. The next four minutes gave a spike to 84° C. and complete solidification of the pot. After a few more minutes in the bath the efflux ended and the pot cooled to 65° C. Ethanol (250 mL) was added, the pot brought to boil, and the contents cooled in a beaker. The crystals which formed were separated by pressure filtration under nitrogen, rinsed with ethanol (50 mL), and dried in a stream of nitrogen to give the product $SO_2Im_2$ (69.5 g, 0.35 moles, 80%) m.p.=140-141° C.

Example 34

Sulfonyldiimidazole. A 300 mL 1-necked roundbottom flask was equipped with a stir egg, charged with $FSO_2Im$ (42 g, 0.28 moles), $Me_3SiIm$ (42 g, 0.3 moles) and triethylamine (5.3 g, 50 mmoles), topped with a condenser and nitrogen blanket, and placed in an oil bath. The pot was stirred magnetically and the bath was slowly raised to 130° C. No efflux of gas was observed, and the pot was stirred another 18 hours at 130° C. The next morning the pot contents were a black solid mass with a small amount of refluxing liquid. This black solid was recrystallized twice from ethanol; the crystals so obtained were separated by pressure filtration under nitrogen and dried in a stream of nitrogen to give the product $SO_2Im_2$ (43.1 g, 0.22 moles, 78%) m.p.=140-141° C.

Example 35

Sulfonyldiimidazole and Fluorosulfonylimidazole. A 500 mL one-necked roundbottom flask was equipped with a stir egg and charged with $Me_3SiIm$ (142.8 g, 1 mole) and DBU (0.33 g, 2 mmoles), sealed, iced, and evacuated to constant pressure (<0.1 kPa). $SO_2F_2$ was introduced to the iced pot at a gated pressure of 93 kPa. After about an hour and a half the pot was checked and found to have risen above 93 kPa and the addition was stopped. The $SO_2F_2$ added was 94 g (0.92 moles). The pot was warmed up and allowed to vent, then distilled at 53° C./2.7 kPa to give $FSO_2Im$ (86 g, 0.57 moles, 57%). The considerable pot mass, 48 g, was recrystallized from ethanol. The crystals which formed were separated by pressure filtration under nitrogen, rinsed with ethanol (50 mL), and dried in a stream of nitrogen to give $SO_2Im_2$ (33 g, 0.17 moles, 33%). M.p.=139-41° C. Combined yield 90% for both products based on $Me_3SiIm$ starting material.

Example 36

Sulfonyldiimidazole. A 500 mL, 3-necked roundbottom flask with a stir egg, rubber seal, thermometer, and gas bubbler was charged with $FSO_2Im$ (70 g, 0.47 moles) and $Me_3SiIm$ (66 g, 0.47 moles), and held in a 50° C. bath throughout the reaction. DBU (two drops, about 0.04 g, 0.3 mmoles) was added and the temperature and gas efflux monitored. The reaction took exactly four hours. The temperature remained at 50-53° C. almost the whole time. Efflux was slow initially. After 36 minutes (53° C.) precipitate appeared. After another hour the efflux rate had increased and reached a peak at the exotherm (55° C.) which lasted about five minutes. The pot contents solidified. After another 15 minutes in the 50° C. bath the pot had dropped to 46° C.

and no more gas efflux was observed. The pot contents were diluted with ethanol (315 mL), brought to boil, poured into a beaker and the clear yellow solution allowed to cool. The crystals which formed were separated by pressure filtration under nitrogen, rinsed with ethanol (40 mL), and dried in a stream of nitrogen to give the product $SO_2Im_2$ (80.5 g, 0.4 moles, 87%). M.p.=140-141° C. A second crop was collected from the concentrated filtrate, 9 g, m.p.=139-140° C. Total yield, 89.5 g, 0.45 moles, 97%.

Example 37

1-(1H-Imidazole-1-sulfonyl)-1H-pyrazole ($ImSO_2Pz$). A 500 mL, 3-necked roundbottom flask with a stir egg, rubber seal, thermometer, and gas bubbler was charged with $FSO_2Im$ (71.3 g, 0.475 moles) and $Me_3SiTz$ (67.5 g, 0.477 moles), and held in a 50° C. bath throughout the reaction. DBU (four drops, about 0.06 g, 0.4 mmoles) was added and the temperature and gas efflux monitored. Efflux was slow and the pot stirred for a day and a half with only a small amount of solid observed. More DBU (0.15 g, 1 mmole) was added with immediate result. The temperature spiked to 79° C. after 13 minutes and cooled to 48° C. after 30 minutes more in the 50° C. bath. After another hour ethanol (200 mL) was added, the pot brought to boil, poured into a beaker and cooled. The crystals which formed were separated by pressure filtration under nitrogen and dried in a stream of nitrogen to give the product $ImSO_2Pz$ (83 g, 0.42 moles, 87%). M.p.=109-110° C. A sample was recrystallized from acetonitrile, m.p.=110-112° C. GCMS m/e 199, 135 (S02-extruded coupling product).

Example 38

Fluorosulfonylimidazole ($FSO_2Im$). A 1 liter 4-necked flask was equipped with a stir egg, thermometer, stoppers, and a vacuum adapter, and charged with $Me_3SiIm$ (235.8 g, 1.68 moles), DBU (0.37 g, 2.5 mmoles) and dichloromethane (250 mL). The pot was cooled with a dry ice-acetone bath to −18° C. and evacuated to constant static pressure (3.9 kPa). $SO_2F_2$ (182 g, 1.78 moles) was added to the magnetically stirred pot at −11 to −18° C. and 80 kPa over 30 minutes, in two portions, the first portion being insufficient. The endpoint was at −15.5° C. and 40 kPa. The pot was warmed, and when the pot pressure equaled atmospheric, the vacuum adapter was replaced with a reflux condenser attached to a bubbler and the pot brought to reflux until the pot temperature had risen to 43° C. The pot was then distilled at 53-54° C./2.7 kPa to give the product $FSO_2Im$ (217 g, 1.45 moles, 86%).

Example 39

Fluorosulfonyltriazole ($FSO_2Tz$). A 500 mL 2-necked flask was equipped with a stir egg, thermometer, and a vacuum adapter, and charged with $Me_3SiTz$ (98 g, 0.69 moles), DBU (0.06 g, 0.4 mmoles) and dichloromethane (250 mL). The pot was cooled with a dry ice-acetone bath to −60° C. and evacuated to constant static pressure (0.4 kPa). $SO_2F_2$ (78 g, 0.76 moles) was added over six minutes to the magnetically stirred pot at −65 to −57° C. and 66-33 kPa. The endpoint pressure then dropped to 21 kPa. The pot was stirred for five minutes at about −60° C., then warmed. The pot pressure rose with the temperature until about −20° C. when it dropped from 45 to 42 kPa, then continued to rise with the temperature. At +13° C. the pressure was atmospheric, and the vacuum outlet was replaced with a still head. After removal of the volatile components, the product $FSO_2Tz$ distilled at 50° C./1.7 kPa (73 g, 0.48 moles, 70%).

Example 40

Fluorosulfonyltriazole ($FSO_2Tz$). A 500 mL 2-necked flask was equipped with a stir egg, thermometer, and a vacuum adapter, and charged with $Me_3SiTz$ (98 g, 0.69 moles), DBU (50 µL, 55 mg, 36 µmoles) and dichloromethane (250 mL). The pot was cooled with a dry ice-acetone bath to −64° C. and evacuated to constant static pressure (0.4 kPa). $SO_2F_2$ (108 g, 1.06 moles) was added over six minutes to the magnetically stirred pot at −64 to −52° C. and 93 kPa. After the endpoint the pot cooled to −69° C. and 22 kPa. The pot was infilled with nitrogen at −69° C., attached to a bubbler, and slowly allowed to warm with stirring for 12 hours. After removal of the volatile components, the product $FSO_2Tz$ distilled at 52-53° C./2.0 kPa. Yield, 92 g (0.6 moles, 87%).

Example 41

Sulfonyldiimidazole. A solution of imidazole (34.04 g, 0.5 moles in 1.00N aqueous NaOH (500 mL) in a 1-necked 1 liter roundbottom flask was concentrated to dryness on a rotary evaporator, then placed under high vacuum and kept for 40 minutes at 200° C./13 Pa using an oil bath. A friable solid was obtained (45 g, 100%). The flask was cooled, infilled with nitrogen and a stir egg added. The pot was closed with a rubber seal, and acetonitrile (500 mL) transferred in via cannula. The seal was quickly replaced with a vacuum adapter and the pot pumped down to 10 kPa when it began to boil. The pot was placed in a water bath at about 20° C., stirred, and $SO_2F_2$ (39 g, 0.38 moles) added over 55 minutes at 93 kPa. The endpoint pressure was 89 kPa. The pot was unsealed, a condenser added, and the pot contents gently warmed to expel most of the excess $SO_2F_2$ gas. The remainder of gas was expelled by a short reflux. The pot was then concentrated to dryness, the contents taken up in ethanol (250 mL) and brought to reflux. The pot contents were then hot filtered, boiled down to 200 mL in an open beaker, and cooled. The crystals which formed were separated by pressure filtration under nitrogen and dried in a stream of nitrogen to give the product as colorless crystals (38 g, 0.19 moles, 77%). Mp=139-140° C.

Example 42

Sulfonylbis(3,5-dimethylpyrazole).
1. Sodium 3,5-dimethylpyrazolate. NaOH (0.5 liters, 1.000 N, 0.5 moles) was added to a 1 L one-necked roundbottom flask, concentrated to about 50 mL on a rotary evaporator and 3,5-dimethylpyrazole (48 g, 0.5 moles) added, followed by 2-methytetrahydrofuran (2-MeTHF, 300 mL), and a large stir egg. The pot was magnetically stirred and brought to reflux with a Dean-Stark trap to remove water. After 70 mL water was removed, another 300 mL 2-MeTHF was added and the pot further refluxed until no more water was drawn off. The pot contents were fractionally distilled to dryness, then held in an oil bath set to 200° C./30 Pa for 75 minutes giving 67 g white solid (59 g calculated) which did not lose more mass after further heating under dynamic vacuum. This solid was used directly in the next step.
2. Sulfonylbis(3,5-dimethylpyrazole). To the solid pot contents of Step 1 was added acetonitrile (500 mL) and magnetically stirred, producing a suspension. The stirred suspension was evacuated to constant static pressure (9.3 kPa). SO$_2$F$_2$ (28 g, 0.27 moles) was added to the pot at 67 kPa over 15 minutes. The pot was then gradually heated to drive off volatile components and filtered while hot through a fritted glass Buchner funnel. This process was inefficient; much solid remained and the filter clogged. The clear liquid which did get through the filter was concentrated on a rotary evaporator to give an oil (28 g) which solidified on cooling. This solid was taken up in acetonitrile and filter pressed under nitrogen through several short silica columns until the eluent was clear. Recrystallization from acetonitrile in a freezer, followed by drying under dynamic vacuum, gave the product as a white semicrystalline solid (7.4 g, 28 mmoles, 6%). M.p. (sealed tube)=98-102° C.; remelted at 98-104° C. GCMS m/e 254. A small amount of dimethylpyrazole was detected in the GC trace.

Example 43

Sulfonyldiimidazole. A 500 mL 1-necked roundbottom flask was charged with FSO$_2$Im (45 g, 0.3 moles), imidazole (22.5 g, 0.33 moles) triethylamine (31 g, 0.3 moles), and acetonitrile (150 mL). The pot was stirred in an oil bath set to 80° C. for 50 minutes, and analyzed by GCMS, which indicated the reaction was mostly complete. The pot was taken out of the bath and let to stir overnight. The next morning a solid precipitate was found. The solid was collected by filtration, stirred with chilled ethanol (200 mL), refiltered and the cake rinsed with a little ethanol. The solid was dried under dynamic vacuum to give the product SO$_2$Im$_2$ (43.5 g, 0.22 moles, 73%) as an amorphous white solid, m.p.=141-141.5° C.

Example 44

Sulfonyldiimidazole. A 600 mL autoclave was charged with imidazole (35 g, 0.51 moles), triethylamine (52 g, 0.51 moles) and dichloromethane (250 mL), sealed, cooled to below −50° C., and evacuated to constant static pressure (1 kPa). SO$_2$F$_2$ (26.8 g, 0.26 moles) was added rapidly from an inverted lecture bottle and the autoclave sealed. The autoclave was brought to 80° C. over 30 minutes and held at 80° C. for an hour. The autoclave was then iced, giving low pressure, and opened. The clear, light yellow liquid from the pot was transferred to a flask and the volatile components removed (0.3 kPa) to give a damp solid (74 g). This solid was washed twice with ethanol (2×50 mL) and dried under dynamic vacuum to give the product SO$_2$Im$_2$ (18.5 g, 93 mmoles, 37%). M.p.=139-142° C.

Example 45

Sulfonyldiimidazole. A 600 mL autoclave was charged with imidazole (70 g, 1 mole), triethylamine (52 g, 0.51 moles) and dichloromethane (250 mL), sealed, cooled to below −50° C., and evacuated to constant static pressure (1 kPa). SO$_2$F$_2$ (27.2 g, 0.27 moles) was added rapidly from an inverted lecture bottle and the autoclave sealed. The autoclave was brought to 80° C. over 25 minutes and held at 80° C. for an hour. The autoclave was then iced, giving low pressure, and opened. The clear, light yellow liquid from the pot was transferred to a flask and the volatile components removed (0.3 kPa) to give a viscous oil with solids (125 g). The oil was taken up in iced ethanol (100 mL) and the solid, free of oil, was collected by filtration. The solid was washed with ethanol (50 mL) and the cake rinsed with ethanol. The resulting white crystalline material so obtained was dried under dynamic vacuum to give the product SO$_2$Im$_2$ (36.5 g, 0.18 moles, 69%). M.p.=139-140° C.

Table 1 summarizes the reaction conditions, the products and the yield of the Examples above.

TABLE 1

| EXAMPLE | REACTANT 1 | REACTANT 2 | SOLVENT | CATALYST (ratio) | T, deg C. (low) | TIME, hours | PRESSURE | PRODUCT | YIELD % |
|---|---|---|---|---|---|---|---|---|---|
| 1 | SO2F2 | imidazole | CH3CN | K2CO3 (1.5) | 50 | 3.0 | low | SO2Im2 | 82 |
| 2 | SO2F2 | imidazole | CH3CN | Na2CO3 | 50 | 3.0 | low | SO2Im2 | 72 |
| 3 | SO2F2 | Me3SiIm | CH2Cl2 | Et3N (0.2) | 25 | 72 | high | FSO2Im | 94 |
| 4 | FSO2Im | imidazole | CH3CN | K2CO3 (1.5) | 50 | 8.0 | low | SO2Im2 | 80 |
| 5 | SO2F2 | Me3SiIm | none | DBU (0.015) | −2 (−25) | 0.5 | high | SO2Im2 | 85 |
| 6 | SO2F2 | Me3SiIm | CH3CN | DBU (0.0025) | 26 (2) | 0.60 | low | SO2Im2 | 92 |
| 7 | SO2F2 | Me3SiIm | CH3CN | no catalyst | 100 (30) |  | high | SO2Im2 | 73 |
| 8 | FSO2Im | Me3SiIm | butyronitrile | DBU (0.002) | DBU | 4.0 | low | SO2Im2 | 85 |
| 9 | SO2F2 | imidazole | CH3CN | Et3N (1) | 80 | 1 | high | SO2Im2 | 40 |
| 10 | SO2F2 | imidazole | CH3CN | DBU (1) | 80 | 2 | low | SO2Im2 | 54 |
| 11 | SO2F2 | Me3SiIm | none | imidazole (0.01) | 20 (12) | 15 | high | FSO2Im | 59 |
| 12 | SO2F2 | Me3SiIm | CH3CN | no catalyst | 25 (17) | 12 | low | FSO2Im | 59 |
| 13 | SO2F2 | Me3SiIm | CH3CN | Et3N (0.01) | 17 (8) | 0.75 | high | FSO2Im | 85 |
| 14 | SO2F2 | Me3SiIm | CH3CN | no catalyst | 14 (1) | 3 | high | FSO2Im | 67 |
| 15 | SO2F2 | Me3SiIm | CH3CN | imidazole (0.1) | 25 | 17 | high | FSO2Im | 60 |
| 16 | SO2F2 | Me3SiIm | CH3CN | imidazole (0.1) | 14 (−3) | 0.6 | high | SO2Im2 | 51 |
| 17 | FSO2Im | Me3SiIm | CH3CN | DBU (0.014) | 53 (20) | 9 | low | SO2Im2 | 88 |
| 18 | SO2F2 | Me3Si(2-MeIm) | CH3CN | DBU (0.002) | 10 (0) | 0.5 | low | SO2(2-MeIm)2 | 86 |
| 19 | SO2F2 | Me3Si(2-MeIm) | CH3CN | Et3N (0.09) | 14 (0) | 18 | high | FSO2(2-MeIm) | 88 |
| 20 | SO2F2 | Me3SiTz | CH3CN | DBU (0.002) | 16 (4) | 0.6 | low | SO2Tz2 | 81 |
| 21 | SO2F2 | Me3SiTz | CH2Cl2 | DBU (0.001) | −11 (−18) | 0.5 | low | SO2Tz2 | 90 |
| 22 | SO2F2 | Na + Tz− | CH3CN | no catalyst | 20 | 0.3 | low | SO2Tz2 | 62 |
| 23 | SO2F2 | Me3SiTz | CH3CN | Et3N (0.09) | −15 (−20) | 1 | low | FSO2Tz | 51 |
| 24 | SO2F2 | Me3SiTz | none | Et3N (0.2) | 25 | 24 | high | FSO2Tz | 66 |
| 25 | SO2F2 | Me3SiIm | CH2Cl2 | DBU (0.004) | 15 (2) | 0.3 | low | FSO2Im | 72 |
| 26 | SO2F2 | Me3SiPz | CH3CN | DBU (0.002) | 18 (2) | 0.25 | low | SO2Pz2 | 81 |

TABLE 1-continued

| EXAMPLE | REACTANT 1 | REACTANT 2 | SOLVENT | CATALYST (ratio) | T, deg C. (low) | TIME, hours | PRESSURE | PRODUCT | YIELD % |
|---|---|---|---|---|---|---|---|---|---|
| 27 | SO2F2 | Me3SiPz | CH3CN | DBU (0.001) | ice bath | 1 | low | SO2Pz2 | 92 |
| 28 | SO2F2 | Me3SiBzTz | CH3CN | DBU (0.002) | ice bath | 0.5 | low | SO2(BzTz)2 | 100 |
| 29 | SO2F2 | Me3SiBzIm | CH3CN | DBU (0.002) | ice bath | 0.6 | low | SO2(BzIm)2 | 95 |
| 30 | SO2F2 | Me3Si(PzMe2) | CH3CN | DBU (0.0015) | 8 (2) | 1 | low | FSO2PzMe2 | 95 |
| 31 | FSO2PzMe2 | Me3SiIm | CH3CN | DBU (0.015) | ambient | ten days | low | ImSO2PzMe | 88 |
| 32 | FSO2Im | Me3SiIm | CH3CN | DBU (0.006) | 42 (10) | 3 | low | SO2Im2 | 94 |
| 33 | FSO2Im | Me3SiIm | none | DBU (0.01) | 84 (40) | 0.5 | low | SO2Im2 | 80 |
| 34 | FSO2Im | Me3SiIm | none | Et3N (0.17) | 130 | 18 | low | SO2Im2 | 78 |
| 35 | SO2F2 | Me3SiIm | none | DBU (0.002) | ice bath | 1.5 | low | FSO2Im | 57 |
| 36 | FSO2Im | Me3SiIm | none | DBU (0.0006) | 55 (50) | 4 | low | SO2Im2 | 97 |
| 37 | FSO2Im | Me3SiPz | none | DBU (0.0008) | 79 (50) | 2 | low | ImSO2Pz | 87 |
| 38 | SO2F2 | Me3SiIm | CH2Cl2 | DBU (0.0015) | −11 (−18) | 0.5 | low | FSO2Im | 86 |
| 39 | SO2F2 | Me3SiTz | CH2Cl2 | DBU (0.006) | −57 (−65) | 1 | low | FSO2Tz | 70 |
| 40 | SO2F2 | Me3SiTz | CH2Cl2 | DBU (0.00005) | −52 (−64) | 12 | low | FSO2Tz | 87 |
| 41 | SO2F2 | Na + Im- | CH3CN | no catalyst | 20 | 1.0 | low | SO2Im2 | 77 |
| 42 | SO2F2 | Na + PzMe2- | CH3CN | no catalyst | ambient | 0.25 | low | SO2(PzMe2)2 | 6 |
| 43 | FSO2Im | imidazole | CH3CN | Et3N (1) | 80 | 1.0 | low | SO2Im2 | 73 |
| 44 | SO2F2 | imidazole | CH2Cl2 | Et3N (1) | 80 | 1.0 | high | SO2Im2 | 37 |
| 45 | SO2F2 | imidazole | CH2Cl2 | Et3N (1) | 80 | 1.0 | high | SO2Im2 | 69 |

Although the subject matter has been described in terms of exemplary embodiments, it is not limited thereto. Rather, the appended claims should be construed broadly, to include other variants and embodiments, which may be made by those skilled in the art.

What is claimed is:

1. A method, comprising:
reacting a N-(fluorosulfonyl)azole (Azole 1-SO$_2$F) having a first azole base structure (Azole 1) with a protic azole or an azole anion compound having a second azole base structure (Azole 2); and
isolating an N,N'-sulfonylbisazole (Azole 1-SO$_2$-Azole 2) wherein the azole anion compound is derived from a N-(trialkylsilyl)azole having a second azole base structure (Azole 2) in the presence of a basic catalyst.

2. The method of claim 1, wherein the first and the second azole base structures are independently selected from the group consisting of imidazole, pyrazole, 1,2,4-triazole, benzimidazole, benzotriazole, indazole, 2-methylimidazole, 2-methylbenzimidazole, and 3,5-dimethylpyrazole.

3. The method of claim 1, wherein the first azole base structure (Azole 1) and the second azole base structure (Azole 2) are the same.

4. The method of claim 1, wherein the N-(trialkylsilyl)azole is an N-(trimethylsilyl)azole.

5. The method of claim 1, wherein the basic catalyst is selected from the group consisting of an anion salt of the protic azole (Azole 2) and a cation of a metal selected from the group consisting of lithium, sodium, potassium, cesium, and magnesium.

6. The method of claim 1, wherein the basic catalyst is an aprotic organic base or the protic azole (Azole 2).

7. The method of claim 1, wherein N-(fluorosulfonyl)azole (Azole 1-SO$_2$F) is reacted with the protic azole or the azole anion compound in the presence of an aprotic solvent.

8. The method of claim 7, wherein the first azole base structure (Azole 1) and the second azole base structure (Azole 2) are imidazole or benzimidazole.

9. A method, comprising:
reacting sulfuryl fluoride (SO$_2$F$_2$) with an azole or an azole anion compound having a first protic azole base structure (Azole 1); and
isolating an N,N'-sulfonylbisazole (Azole 1-SO$_2$-Azole 1).

10. The method of claim 9, wherein the first azole base structure is selected from the group consisting of imidazole, pyrazole, 1,2,4-triazole, benzimidazole, benzotriazole, indazole, 2-methylimidazole, 2-methylbenzimidazole, and 3,5-dimethylpyrazole.

11. The method of claim 9, wherein the azole anion compound is an azole anion salt having an ion of a metal selected from the group consisting of lithium, sodium, potassium, cesium, and magnesium.

12. The method of claim 9, wherein the azole anion compound is derived from a protic azole and a metal carbonate, the metal being selected from the group consisting of lithium, sodium, potassium, cesium, and magnesium.

13. The method of claim 9, wherein the azole anion compound is derived from a protic azole and an aprotic base, or a protic azole as the base.

14. The method of claim 9, wherein the azole anion compound is derived from a N-(trialkylsilyl)azole having a first azole base structure in the presence of a basic catalyst.

15. A method, comprising:
reacting sulfuryl fluoride (SO$_2$F$_2$) with a N-(trialkylsilyl)azole having a first azole base structure (Azole 1); and
isolating a N-(fluorosulfonyl)azole (Azole 1-SO$_2$F).

16. The method of claim 15, wherein the first azole base structure is selected from the group consisting of imidazole, pyrazole, 1,2,4-triazole, benzimidazole, benzotriazole, indazole, 2-methylimidazole, 2-methylbenzimidazole, and 3,5-dimethylpyrazole.

17. The method of claim 15, wherein the N-(trialkylsilyl)azole is an N-(trimethylsilyl)azole.

18. The method of claim 15, where the reaction is performed in the presence of an aprotic solvent or a basic catalyst or both.

19. The method of claim 18, wherein the basic catalyst is an aprotic organic base, or the protic Azole 1 as a base.

20. The method of claim 18, wherein the basic catalyst is selected from the group consisting of an anion salt of a protic azole (Azole 1) and an ion of a metal selected from the group consisting of lithium, sodium, potassium, cesium, and magnesium.

21. The method of claim 17, further comprising:
reacting the N-(fluorosulfonyl)azole (Azole 1-$SO_2F$) with a second N-(trialkylsilyl)azole or an azole anion salt having a second azole base structure (Azole 2) to provide an N,N'-sulfonylbisazole (Azole 1-$SO_2$-Azole 2).

22. The method of claim 21, wherein the first and the second azole base structures are the same, and sulfuryl fluoride ($SO_2F_2$) is reacted with the first N-(trialkylsilyl)azole in one pot directly to provide a symmetric sulfonylbisazole.

23. The method of claim 9, wherein $SO_2F_2$ is added to a protic azole in the presence of an aprotic base and in an aprotic solvent.

24. The method of claim 23, wherein the aprotic base is sodium carbonate or potassium carbonate.

25. The method of claim 23, wherein the aprotic base is an aprotic organic base.

26. The method of claim 25, wherein the aprotic organic base is triethylamine.

27. The method of claim 23, wherein the aprotic solvent is acetonitrile.

28. The method of claim 23, wherein said azole is imidazole.

* * * * *